US009400285B2

(12) United States Patent
Ochranek et al.

(10) Patent No.: US 9,400,285 B2
(45) Date of Patent: Jul. 26, 2016

(54) AUTOMATED DIAGNOSTIC ANALYZERS HAVING VERTICALLY ARRANGED CAROUSELS AND RELATED METHODS

(71) Applicants: Abbott Laboratories, Abbott Park, IL (US); Toshiba Medical Systems Corporation, Otawara-shi (JP)

(72) Inventors: Brian L. Ochranek, Abbott Park, IL (US); David C. Arnquist, Abbott Park, IL (US); Takehiko Oonuma, Otawara (JP); Hirotoshi Tahara, Otawara (JP); Naoto Sato, Otawara (JP)

(73) Assignees: Abbot Laboratories, Abbott Park, IL (US); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/213,018

(22) Filed: Mar. 14, 2014

(65) Prior Publication Data
US 2014/0273245 A1    Sep. 18, 2014

Related U.S. Application Data

(60) Provisional application No. 61/794,060, filed on Mar. 15, 2013.

(51) Int. Cl.
*G01N 35/02*  (2006.01)
*G01N 35/04*  (2006.01)

(52) U.S. Cl.
CPC .............. *G01N 35/025* (2013.01); *G01N 35/04* (2013.01); *G01N 35/02* (2013.01); *Y10T 436/11* (2015.01); *Y10T 436/119163* (2015.01)

(58) Field of Classification Search
CPC ..... G01N 35/025; G01N 35/02; G01N 35/04; G01N 35/00; Y10T 436/119163; Y10T 436/11; Y10T 436/00
USPC .............................. 436/54, 43; 422/64, 63, 50
See application file for complete search history.

(56) References Cited

U.S. PATENT DOCUMENTS 3,449,959 A    6/1969    Grimshaw
3,451,433 A    6/1969    Cunningham et al.
(Continued)

FOREIGN PATENT DOCUMENTS

CN    102520200    6/2012
EP    0576291    12/1993
(Continued)

OTHER PUBLICATIONS

International Search Report and Written Opinion, issued by the International Searching Authority in connection with International patent application No. PCT/US2013/078041, mailed on Sep. 19, 2014, 16 pages.
(Continued)

*Primary Examiner* — Christine T Mui
(74) *Attorney, Agent, or Firm* — Hanley, Flight & Zimmerman, LLC

(57) ABSTRACT

Example automated diagnostic analyzers and methods for using the same are disclosed herein. An example apparatus described herein includes a first carousel rotatably coupled to a base and having a first axis of rotation. The example apparatus includes a second carousel rotatably coupled to the base and vertically spaced over the first carousel such that at least a portion of the second carousel is disposed over the first carousel. In the example apparatus, the second carousel has a second axis of rotation and a plurality of vessels. The example apparatus also includes a pipetting mechanism offset from the second axis of rotation. The example pipetting mechanism is to access the first carousel and the second carousel.

41 Claims, 9 Drawing Sheets

(56) References Cited

U.S. PATENT DOCUMENTS

| | | |
|---|---|---|
| 3,484,206 A | 12/1969 | Loebl |
| 4,738,825 A | 4/1988 | Kelln et al. |
| 4,774,055 A | 9/1988 | Wakatake et al. |
| 4,808,380 A | 2/1989 | Minekane |
| 4,848,917 A | 7/1989 | Benin et al. |
| 4,849,177 A | 7/1989 | Jordan |
| 4,906,433 A | 3/1990 | Minekane |
| 5,037,612 A | 8/1991 | Takahashi |
| 5,051,238 A | 9/1991 | Umetsu et al. |
| 5,071,625 A | 12/1991 | Kelln et al. |
| 5,077,013 A | 12/1991 | Guigan |
| 5,154,896 A | 10/1992 | Mochida et al. |
| 5,244,633 A | 9/1993 | Jakubowicz et al. |
| 5,250,440 A | 10/1993 | Kelln et al. |
| 5,266,268 A | 11/1993 | Antocci et al. |
| 5,270,212 A | 12/1993 | Horiuchi et al. |
| 5,311,426 A | 5/1994 | Donohue et al. |
| 5,314,825 A | 5/1994 | Weyrauch et al. |
| 5,352,612 A | 10/1994 | Huber et al. |
| 5,358,691 A | 10/1994 | Clark et al. |
| 5,360,597 A | 11/1994 | Jakubowicz et al. |
| 5,419,871 A | 5/1995 | Muszak et al. |
| 5,422,271 A | 6/1995 | Chen et al. |
| 5,424,036 A | 6/1995 | Ushikubo |
| 5,424,212 A | 6/1995 | Pinsl-Ober et al. |
| 5,434,083 A | 7/1995 | Mitsumaki et al. |
| 5,439,646 A | 8/1995 | Tanimizu et al. |
| 5,443,791 A | 8/1995 | Cathcart et al. |
| 5,445,794 A | 8/1995 | Wihlborg |
| 5,447,687 A | 9/1995 | Lewis et al. |
| 5,455,175 A | 10/1995 | Wittwer et al. |
| 5,460,780 A | 10/1995 | Devaney, Jr. et al. |
| 5,460,968 A | 10/1995 | Yoshida et al. |
| 5,462,715 A | 10/1995 | Koch et al. |
| 5,466,574 A | 11/1995 | Liberti et al. |
| 5,470,744 A | 11/1995 | Astle |
| 5,482,834 A | 1/1996 | Gillespie |
| 5,482,839 A | 1/1996 | Ashihara et al. |
| 5,482,861 A | 1/1996 | Clark et al. |
| 5,518,693 A | 5/1996 | Tomasso et al. |
| 5,525,300 A | 6/1996 | Danssaert et al. |
| 5,527,673 A | 6/1996 | Reinhartz et al. |
| 5,536,475 A | 7/1996 | Moubayed et al. |
| 5,536,481 A | 7/1996 | Mabire et al. |
| 5,538,849 A | 7/1996 | Uematsu et al. |
| 5,538,976 A | 7/1996 | Okada et al. |
| 5,548,826 A | 8/1996 | Sayers |
| 5,558,839 A | 9/1996 | Matte et al. |
| 5,559,002 A | 9/1996 | Uzan et al. |
| 5,567,595 A | 10/1996 | Kok |
| 5,571,325 A | 11/1996 | Ueyama et al. |
| 5,571,481 A | 11/1996 | Powell et al. |
| 5,575,976 A | 11/1996 | Choperena et al. |
| 5,576,215 A | 11/1996 | Burns et al. |
| 5,578,269 A | 11/1996 | Yaremko et al. |
| 5,578,270 A | 11/1996 | Reichler et al. |
| 5,580,524 A | 12/1996 | Forrest et al. |
| 5,582,796 A | 12/1996 | Carey et al. |
| 5,585,068 A | 12/1996 | Panetz et al. |
| 5,587,129 A | 12/1996 | Kurosaki et al. |
| 5,589,137 A | 12/1996 | Markin et al. |
| 5,595,707 A | 1/1997 | Copeland et al. |
| 5,599,501 A | 2/1997 | Carey et al. |
| 5,611,994 A | 3/1997 | Bailey et al. |
| 5,620,898 A | 4/1997 | Yaremko et al. |
| 5,632,399 A | 5/1997 | Palmieri et al. |
| 5,637,275 A | 6/1997 | Carey et al. |
| 5,639,425 A | 6/1997 | Komiyama et al. |
| 5,650,327 A | 7/1997 | Copeland et al. |
| 5,653,940 A | 8/1997 | Carey et al. |
| 5,654,199 A | 8/1997 | Copeland et al. |
| 5,654,200 A | 8/1997 | Copeland et al. |
| 5,656,493 A | 8/1997 | Mullis et al. |
| 5,658,532 A | 8/1997 | Kurosaki et al. |
| 5,658,799 A | 8/1997 | Choperena et al. |
| 5,670,114 A | 9/1997 | Sakazume et al. |
| 5,670,120 A | 9/1997 | Degenhardt et al. |
| 5,670,375 A | 9/1997 | Seaton et al. |
| 5,677,188 A | 10/1997 | Mitsumaki et al. |
| 5,679,309 A | 10/1997 | Bell |
| 5,681,530 A | 10/1997 | Kuster et al. |
| 5,682,026 A | 10/1997 | Auclair et al. |
| 5,686,046 A | 11/1997 | Malek et al. |
| 5,693,292 A | 12/1997 | Choperena et al. |
| 5,698,450 A | 12/1997 | Ringrose et al. |
| 5,702,950 A | 12/1997 | Tajima |
| 5,705,062 A | 1/1998 | Knobel |
| 5,714,380 A | 2/1998 | Neri et al. |
| 5,716,583 A | 2/1998 | Smethers et al. |
| 5,717,148 A | 2/1998 | Ely et al. |
| 5,720,377 A | 2/1998 | Lapeus et al. |
| 5,720,923 A | 2/1998 | Haff et al. |
| 5,721,141 A | 2/1998 | Babson et al. |
| 5,723,092 A | 3/1998 | Babson et al. |
| 5,730,938 A | 3/1998 | Carbonari et al. |
| 5,730,939 A | 3/1998 | Kurumada et al. |
| 5,736,101 A | 4/1998 | Gianino |
| 5,736,105 A | 4/1998 | Astle |
| 5,736,413 A | 4/1998 | Uzan et al. |
| 5,738,827 A | 4/1998 | Marquiss |
| 5,741,461 A | 4/1998 | Takahashi et al. |
| 5,741,708 A | 4/1998 | Carey et al. |
| 5,746,977 A | 5/1998 | Imai et al. |
| 5,746,978 A | 5/1998 | Bienhaus et al. |
| 5,748,978 A | 5/1998 | Narayan et al. |
| 5,750,338 A | 5/1998 | Collins et al. |
| 5,762,872 A | 6/1998 | Bühler et al. |
| 5,762,873 A | 6/1998 | Fanning et al. |
| 5,773,268 A | 6/1998 | Korenberg et al. |
| 5,773,296 A | 6/1998 | Montalbano et al. |
| 5,773,662 A | 6/1998 | Imai et al. |
| 5,779,981 A | 7/1998 | Danssaert et al. |
| 5,786,182 A | 7/1998 | Catanzariti et al. |
| 5,789,252 A | 8/1998 | Fujita et al. |
| 5,795,547 A | 8/1998 | Moser et al. |
| 5,795,784 A | 8/1998 | Arnquist et al. |
| 5,807,523 A | 9/1998 | Watts et al. |
| 5,814,277 A | 9/1998 | Bell et al. |
| 5,816,998 A | 10/1998 | Silverstolpe et al. |
| 5,826,129 A | 10/1998 | Hasebe et al. |
| 5,827,478 A | 10/1998 | Carey et al. |
| 5,827,479 A | 10/1998 | Yamazaki et al. |
| 5,827,653 A | 10/1998 | Sammes et al. |
| 5,837,195 A | 11/1998 | Malek et al. |
| 5,843,376 A | 12/1998 | Ishihara et al. |
| 5,846,491 A | 12/1998 | Choperena et al. |
| 5,849,247 A | 12/1998 | Uzan et al. |
| 5,855,847 A | 1/1999 | Oonuma et al. |
| 5,856,194 A | 1/1999 | Arnquist et al. |
| 5,863,506 A | 1/1999 | Farren |
| 5,876,668 A | 3/1999 | Kawashima et al. |
| 5,876,670 A | 3/1999 | Mitsumaki et al. |
| 5,882,594 A | 3/1999 | Kawaguchi et al. |
| 5,882,596 A | 3/1999 | Breeser et al. |
| 5,882,918 A | 3/1999 | Goffe |
| 5,885,353 A | 3/1999 | Strodtbeck et al. |
| 5,885,529 A | 3/1999 | Babson et al. |
| 5,885,530 A | 3/1999 | Babson et al. |
| 5,888,454 A | 3/1999 | Leistner et al. |
| 5,897,783 A | 4/1999 | Howe et al. |
| 5,902,549 A | 5/1999 | Mimura et al. |
| 5,919,622 A | 7/1999 | Macho et al. |
| 5,928,952 A | 7/1999 | Hutchins et al. |
| 5,935,522 A | 8/1999 | Swerdlow et al. |
| 5,948,691 A | 9/1999 | Ekiriwang et al. |
| 5,955,373 A | 9/1999 | Hutchins et al. |
| 5,958,763 A | 9/1999 | Goffe |
| 5,972,295 A | 10/1999 | Hanawa et al. |
| 5,985,215 A | 11/1999 | Sakazume et al. |
| 5,985,670 A | 11/1999 | Markin |
| 5,985,671 A | 11/1999 | Leistner et al. |
| 5,985,672 A | 11/1999 | Kegelman et al. |
| 5,988,869 A | 11/1999 | Davidson et al. |
| 6,019,945 A | 2/2000 | Ohishi et al. |

(56) References Cited

U.S. PATENT DOCUMENTS

| | | |
|---|---|---|
| 6,027,691 A | 2/2000 | Watts et al. |
| 6,033,574 A | 3/2000 | Siddiqi |
| 6,033,880 A | 3/2000 | Haff et al. |
| 6,042,786 A | 3/2000 | Oonuma et al. |
| 6,043,880 A | 3/2000 | Andrews et al. |
| 6,051,101 A | 4/2000 | Ohtani et al. |
| 6,056,923 A | 5/2000 | Diamond et al. |
| 6,060,022 A | 5/2000 | Pang et al. |
| 6,063,340 A | 5/2000 | Lewis et al. |
| 6,068,393 A | 5/2000 | Hutchins et al. |
| 6,068,978 A | 5/2000 | Zaun et al. |
| 6,071,395 A | 6/2000 | Lange |
| 6,071,477 A | 6/2000 | Auclair et al. |
| 6,074,615 A | 6/2000 | Lewis et al. |
| 6,080,364 A | 6/2000 | Mimura et al. |
| 6,086,827 A | 7/2000 | Horner et al. |
| 6,096,272 A | 8/2000 | Clark et al. |
| 6,103,193 A | 8/2000 | Iwahashi et al. |
| 6,106,781 A | 8/2000 | Rosenberg |
| 6,110,676 A | 8/2000 | Coull et al. |
| 6,110,678 A | 8/2000 | Weisburg et al. |
| 6,117,392 A | 9/2000 | Hanawa et al. |
| 6,117,398 A | 9/2000 | Bienhaus et al. |
| 6,117,683 A | 9/2000 | Kodama et al. |
| 6,143,578 A | 11/2000 | Bendele et al. |
| 6,146,592 A | 11/2000 | Kawashima et al. |
| 6,156,565 A | 12/2000 | Maes et al. |
| 6,165,778 A | 12/2000 | Kedar |
| 6,174,670 B1 | 1/2001 | Wittwer et al. |
| 6,232,079 B1 | 5/2001 | Wittwer et al. |
| 6,245,514 B1 | 6/2001 | Wittwer et al. |
| 6,261,521 B1 | 7/2001 | Mimura et al. |
| 6,267,927 B1 | 7/2001 | Pomar Longedo et al. |
| 6,277,332 B1 | 8/2001 | Sucholeiki |
| 6,293,750 B1 | 9/2001 | Cohen et al. |
| 6,299,567 B1 | 10/2001 | Forrest et al. |
| 6,300,068 B1 | 10/2001 | Burg et al. |
| 6,300,138 B1 | 10/2001 | Gleason et al. |
| 6,319,718 B1 | 11/2001 | Matsubara et al. |
| 6,332,636 B1 | 12/2001 | Cohen et al. |
| 6,335,166 B1 | 1/2002 | Ammann et al. |
| 6,337,050 B1 | 1/2002 | Takahashi et al. |
| 6,352,861 B1 | 3/2002 | Copeland et al. |
| 6,374,982 B1 | 4/2002 | Cohen et al. |
| 6,375,898 B1 | 4/2002 | Ulrich |
| 6,377,342 B1 | 4/2002 | Coeurveille |
| 6,386,749 B1 | 5/2002 | Watts et al. |
| 6,399,952 B1 | 6/2002 | Maher et al. |
| 6,436,349 B1 | 8/2002 | Carey et al. |
| 6,444,171 B1 | 9/2002 | Sakazume et al. |
| 6,455,325 B1 | 9/2002 | Tajima |
| 6,461,570 B2 | 10/2002 | Ishihara |
| 6,472,217 B1 | 10/2002 | Richards et al. |
| 6,498,037 B1 | 12/2002 | Carey et al. |
| 6,503,751 B2 | 1/2003 | Hugh |
| 6,509,193 B1 | 1/2003 | Tajima |
| 6,517,782 B1 | 2/2003 | Horner et al. |
| 6,517,783 B2 | 2/2003 | Horner et al. |
| 6,521,183 B1 | 2/2003 | Burri et al. |
| 6,522,976 B2 | 2/2003 | Shiba et al. |
| 6,551,833 B1 | 4/2003 | Lehtinen et al. |
| 6,562,298 B1 | 5/2003 | Arnquist et al. |
| 6,569,627 B2 | 5/2003 | Wittwer et al. |
| 6,579,717 B1 | 6/2003 | Matsubara et al. |
| 6,586,234 B1 | 7/2003 | Burg et al. |
| 6,592,818 B2 | 7/2003 | Ishihara et al. |
| 6,597,450 B1 | 7/2003 | Andrews et al. |
| 6,599,749 B1 | 7/2003 | Kodama et al. |
| 6,605,213 B1 | 8/2003 | Ammann et al. |
| 6,632,654 B1 | 10/2003 | Gebrian et al. |
| 6,709,634 B1 | 3/2004 | Okada et al. |
| 6,723,288 B2 | 4/2004 | Devlin, Sr. et al. |
| 6,733,728 B1 | 5/2004 | Mimura et al. |
| 6,752,967 B2 | 6/2004 | Farina et al. |
| 6,764,649 B2 | 7/2004 | Ammann |
| 6,764,650 B2 | 7/2004 | Takahashi et al. |
| 6,776,961 B2 | 8/2004 | Lindsey et al. |
| 6,780,617 B2 | 8/2004 | Chen |
| 6,787,338 B2 | 9/2004 | Wittwer et al. |
| 6,825,921 B1 | 11/2004 | Modlin et al. |
| 6,827,901 B2 | 12/2004 | Copeland et al. |
| 6,866,821 B2 | 3/2005 | Friedlander et al. |
| 6,878,343 B2 | 4/2005 | Sklar et al. |
| 6,890,742 B2 | 5/2005 | Ammann et al. |
| 6,911,327 B2 | 6/2005 | McMillan et al. |
| 6,919,058 B2 | 7/2005 | Andersson et al. |
| 6,919,175 B1 | 7/2005 | Bienhaus et al. |
| 6,924,152 B2 | 8/2005 | Matsubara et al. |
| 6,943,029 B2 | 9/2005 | Coepland et al. |
| 6,958,130 B1 | 10/2005 | Gicquel et al. |
| 7,011,792 B2 | 3/2006 | Mimura et al. |
| 7,028,831 B2 | 4/2006 | Veiner |
| 7,029,922 B2 | 4/2006 | Miller |
| 7,033,820 B2 | 4/2006 | Ammann |
| 7,081,226 B1 | 7/2006 | Wittwer et al. |
| 7,105,351 B2 | 9/2006 | Matsubara et al. |
| 7,115,090 B2 | 10/2006 | Lagarde |
| 7,115,384 B2 | 10/2006 | Clark et al. |
| 7,118,892 B2 | 10/2006 | Ammann et al. |
| 7,118,918 B2 | 10/2006 | Copeland et al. |
| 7,118,982 B2 | 10/2006 | Govyadinov et al. |
| 7,132,082 B2 | 11/2006 | Aviles et al. |
| 7,135,145 B2 | 11/2006 | Ammann et al. |
| 7,138,091 B2 | 11/2006 | Lee et al. |
| 7,141,213 B1 | 11/2006 | Pang et al. |
| 7,160,998 B2 | 1/2007 | Wittwer et al. |
| 7,169,356 B2 | 1/2007 | Gebrian et al. |
| 7,171,863 B2 | 2/2007 | Tamura et al. |
| 7,182,912 B2 | 2/2007 | Carey et al. |
| 7,217,513 B2 | 5/2007 | Parameswaran et al. |
| 7,220,589 B2 | 5/2007 | Richards et al. |
| 7,250,303 B2 | 7/2007 | Jakubowicz et al. |
| 7,264,111 B2 | 9/2007 | Veiner |
| 7,267,795 B2 | 9/2007 | Ammann et al. |
| 7,270,783 B2 | 9/2007 | Takase et al. |
| 7,273,749 B1 | 9/2007 | Wittwer et al. |
| 7,276,208 B2 | 10/2007 | Sevigny et al. |
| 7,303,139 B1 | 12/2007 | Rudloff |
| 7,331,474 B2 | 2/2008 | Veiner et al. |
| 7,341,691 B2 | 3/2008 | Tamura et al. |
| 7,360,984 B1 | 4/2008 | Sugiyama et al. |
| 7,361,305 B2 | 4/2008 | Mimura et al. |
| 7,381,370 B2 | 6/2008 | Chow et al. |
| 7,384,600 B2 | 6/2008 | Burns et al. |
| 7,390,458 B2 | 6/2008 | Burow et al. |
| 7,396,509 B2 | 7/2008 | Burns |
| 7,402,281 B2 | 7/2008 | Huynh-Ba et al. |
| 7,407,627 B1 | 8/2008 | Rosenberg et al. |
| 7,482,143 B2 | 1/2009 | Ammann et al. |
| 7,524,652 B2 | 4/2009 | Ammann et al. |
| 7,560,255 B2 | 7/2009 | Ammann et al. |
| 7,560,256 B2 | 7/2009 | Ammann et al. |
| 7,575,937 B2 | 8/2009 | Wiggli et al. |
| 7,611,675 B2 | 11/2009 | Sevigny et al. |
| 7,622,078 B2 | 11/2009 | Pagés Pinyol |
| 7,638,337 B2 | 12/2009 | Ammann et al. |
| 7,641,855 B2 | 1/2010 | Farina et al. |
| 7,666,602 B2 | 2/2010 | Ammann et al. |
| 7,666,681 B2 | 2/2010 | Ammann et al. |
| 7,670,553 B2 | 3/2010 | Babson |
| 7,670,554 B2 | 3/2010 | Chow et al. |
| 7,670,832 B2 | 3/2010 | Wittwer et al. |
| 7,700,042 B2 | 4/2010 | Matsumoto et al. |
| 7,700,043 B2 | 4/2010 | Mimura et al. |
| 7,731,414 B2 | 6/2010 | Vincent et al. |
| 7,731,898 B2 | 6/2010 | Burkhardt et al. |
| 7,745,205 B2 | 6/2010 | Wittwer et al. |
| 7,749,441 B2 | 7/2010 | Hanawa et al. |
| 7,785,534 B2 | 8/2010 | Watari |
| 7,815,858 B2 | 10/2010 | Sevigny et al. |
| 7,827,874 B2 | 11/2010 | Tsujimura et al. |
| 7,837,452 B2 | 11/2010 | Ignatiev et al. |
| 7,842,237 B1 | 11/2010 | Shibuya et al. |
| 7,842,504 B2 | 11/2010 | Devlin, Sr. |

(56) References Cited

U.S. PATENT DOCUMENTS

| | | |
|---|---|---|
| 7,850,914 B2 | 12/2010 | Veiner et al. |
| 7,854,892 B2 | 12/2010 | Veiner et al. |
| 7,855,084 B2 | 12/2010 | Jakubowicz et al. |
| 7,858,032 B2 | 12/2010 | Le Comte et al. |
| 7,867,777 B2 | 1/2011 | Aviles et al. |
| 7,910,294 B2 | 3/2011 | Karlsen |
| 7,939,036 B2 | 5/2011 | Burkhardt et al. |
| 7,941,904 B2 | 5/2011 | Smith |
| 7,943,100 B2 | 5/2011 | Rousseau |
| 7,947,225 B2 | 5/2011 | Itoh |
| 7,951,329 B2 | 5/2011 | Malyarov et al. |
| 7,964,140 B2 | 6/2011 | Watari |
| 7,985,375 B2 | 7/2011 | Edens et al. |
| 7,998,409 B2 | 8/2011 | Veiner et al. |
| 7,998,432 B2 | 8/2011 | Rousseau |
| 7,998,751 B2 | 8/2011 | Evers et al. |
| 8,003,050 B2 | 8/2011 | Burkhardt et al. |
| 8,012,419 B2 | 9/2011 | Ammann et al. |
| 8,038,941 B2 | 10/2011 | Devlin, Sr. |
| 8,038,942 B2 | 10/2011 | Pang et al. |
| 8,047,086 B2 | 11/2011 | Smith |
| 8,066,943 B2 | 11/2011 | Kegelman et al. |
| 8,071,053 B2 | 12/2011 | Matsuzaki et al. |
| 8,097,211 B2 | 1/2012 | Hamada et al. |
| 8,114,351 B2 | 2/2012 | Degenhardt et al. |
| 8,119,080 B2 | 2/2012 | Wiggli et al. |
| 8,137,620 B2 | 3/2012 | Ammann et al. |
| 8,142,740 B2 | 3/2012 | Self et al. |
| 8,147,777 B2 | 4/2012 | Schacher et al. |
| 8,153,061 B2 | 4/2012 | Walters et al. |
| 8,154,899 B2 | 4/2012 | Degroot |
| 8,158,058 B2 | 4/2012 | Shiba et al. |
| 8,161,831 B2 | 4/2012 | Fukuma |
| 8,163,239 B2 | 4/2012 | Fujita |
| 8,178,043 B2 | 5/2012 | Burkhardt et al. |
| 8,187,558 B2 | 5/2012 | Jacobs et al. |
| 8,192,992 B2 | 6/2012 | Ammann et al. |
| 8,221,682 B2 | 7/2012 | Ammann et al. |
| 8,226,387 B2 | 7/2012 | Ignatiev |
| 8,234,941 B2 | 8/2012 | Fukuda et al. |
| 8,257,650 B2 | 9/2012 | Chow et al. |
| 8,257,664 B2 | 9/2012 | Ogusu |
| 8,262,994 B2 | 9/2012 | Hamada et al. |
| 8,262,999 B2 | 9/2012 | Kaneblei et al. |
| 8,266,973 B2 | 9/2012 | Maeda et al. |
| 8,293,191 B2 | 10/2012 | Kohara et al. |
| 8,309,358 B2 | 11/2012 | Ammann et al. |
| 8,318,500 B2 | 11/2012 | Ammann et al. |
| 8,329,101 B2 | 12/2012 | Fujita |
| 8,333,936 B2 | 12/2012 | Miyashita et al. |
| 8,337,753 B2 | 12/2012 | Ammann et al. |
| 8,343,423 B2 | 1/2013 | Mori et al. |
| 8,343,754 B2 | 1/2013 | Wittwer et al. |
| 8,343,770 B2 | 1/2013 | Hamada et al. |
| 8,354,078 B2 | 1/2013 | Shohmi et al. |
| 8,355,132 B2 | 1/2013 | Xia et al. |
| 8,356,525 B2 | 1/2013 | Hamada et al. |
| 8,357,538 B2 | 1/2013 | Self et al. |
| 8,366,997 B2 | 2/2013 | Degroot |
| 8,383,039 B2 | 2/2013 | Zhou et al. |
| 8,431,079 B2 | 4/2013 | Rosenberg et al. |
| 8,501,496 B2 | 8/2013 | Zuk et al. |
| 8,545,757 B2 | 10/2013 | Utsugi et al. |
| 8,556,564 B2 | 10/2013 | Miller |
| 9,274,133 B2 | 3/2016 | Kraemer et al. |
| 2002/0155590 A1 | 10/2002 | Gebrian et al. |
| 2002/0164807 A1 | 11/2002 | Itaya et al. |
| 2004/0134750 A1 | 7/2004 | Luoma, II |
| 2005/0014285 A1 | 1/2005 | Miller |
| 2005/0220670 A1 | 10/2005 | Palmieri et al. |
| 2005/0249634 A1 | 11/2005 | Devlin, Sr. |
| 2006/0159587 A1 | 7/2006 | Fechtner et al. |
| 2006/0263248 A1 | 11/2006 | Gomm et al. |
| 2006/0286004 A1 | 12/2006 | Jacobs et al. |
| 2007/0010019 A1 | 1/2007 | Luoma, II |
| 2007/0059209 A1 | 3/2007 | Pang et al. |
| 2007/0092390 A1 | 4/2007 | Ignatiev et al. |
| 2007/0172902 A1 | 7/2007 | Zhang et al. |
| 2008/0145939 A1 | 6/2008 | Jakubowicz et al. |
| 2009/0017491 A1 | 1/2009 | Lemme et al. |
| 2009/0148345 A1 | 6/2009 | Hamazumi et al. |
| 2009/0227033 A1 | 9/2009 | Hamada et al. |
| 2009/0258414 A1 | 10/2009 | Wittwer et al. |
| 2010/0111765 A1 | 5/2010 | Gomm et al. |
| 2010/0126286 A1 | 5/2010 | Self et al. |
| 2010/0187253 A1 | 7/2010 | Vincent et al. |
| 2010/0205139 A1 | 8/2010 | Xia et al. |
| 2010/0276445 A1 | 11/2010 | Jacobs et al. |
| 2010/0330609 A1 | 12/2010 | Nagai et al. |
| 2010/0332144 A1 | 12/2010 | Nagai et al. |
| 2011/0044834 A1 | 2/2011 | Ignatiev |
| 2011/0097240 A1 | 4/2011 | Yamashita et al. |
| 2011/0157580 A1 | 6/2011 | Nogami et al. |
| 2011/0293475 A1 | 12/2011 | Rosenberg et al. |
| 2011/0312082 A1 | 12/2011 | Silverbrook et al. |
| 2012/0039748 A1 | 2/2012 | Mimura et al. |
| 2012/0039771 A1 | 2/2012 | Utsugi et al. |
| 2012/0114526 A1 | 5/2012 | Watanabe et al. |
| 2012/0156764 A1 | 6/2012 | Kondo |
| 2012/0183438 A1 | 7/2012 | Shiba et al. |
| 2012/0218854 A1 | 8/2012 | Behringer et al. |
| 2012/0258004 A1 | 10/2012 | Ignatiev et al. |
| 2012/0294763 A1 | 11/2012 | Fukuda et al. |
| 2012/0301359 A1 | 11/2012 | Kraemer et al. |
| 2013/0017535 A1 | 1/2013 | Frey et al. |
| 2013/0064737 A1 | 3/2013 | Mori et al. |
| 2013/0065797 A1 | 3/2013 | Silbert et al. |
| 2013/0078617 A1 | 3/2013 | Ueda et al. |
| 2013/0089464 A1 | 4/2013 | Sakashita et al. |
| 2013/0112014 A1 | 5/2013 | Hamada et al. |
| 2013/0125675 A1 | 5/2013 | Muller et al. |
| 2013/0280129 A1 | 10/2013 | Watanabe et al. |
| 2013/0280130 A1 | 10/2013 | Sarwar et al. |
| 2013/0323758 A1 | 12/2013 | Oguri et al. |
| 2015/0079695 A1 | 3/2015 | Pollack et al. |

FOREIGN PATENT DOCUMENTS

| | | |
|---|---|---|
| EP | 0779514 | 6/1997 |
| EP | 0871892 | 6/1997 |
| EP | 0831330 | 3/1998 |
| EP | 1414573 | 3/2003 |
| EP | 2068154 | 6/2009 |
| EP | 2362228 | 8/2011 |
| JP | 357019667 | 2/1982 |
| JP | 359116047 | 7/1984 |
| JP | 61095248 | 5/1986 |
| JP | 05026883 | 2/1993 |
| JP | 406027004 | 2/1994 |
| JP | 407181129 | 7/1995 |
| JP | H1062432 | 3/1998 |
| JP | 03582240 | 10/2004 |
| JP | 2005128037 | 5/2005 |
| JP | 2005533641 | 10/2005 |
| JP | 2008224439 | 9/2008 |
| JP | 2008309661 | 12/2008 |
| JP | 2009031204 | 2/2009 |
| JP | 2009145202 | 7/2009 |
| JP | 2010217047 | 9/2010 |
| JP | 2011149832 | 8/2011 |
| JP | 2012021926 | 2/2012 |
| JP | 2012132721 | 7/2012 |
| JP | 2012173180 | 9/2012 |
| JP | 2012189611 | 10/2012 |
| JP | 2012233923 | 11/2012 |
| JP | 2012251804 | 12/2012 |
| JP | 2012251909 | 12/2012 |
| JP | 2012255664 | 12/2012 |
| JP | 05178891 | 4/2013 |
| WO | 9315408 | 8/1993 |
| WO | 9722006 | 6/1997 |
| WO | 03018195 | 3/2003 |
| WO | 2010095375 | 8/2010 |
| WO | 2010106885 | 9/2010 |

(56) References Cited

FOREIGN PATENT DOCUMENTS

| WO | 2010026837 | 11/2010 |
|----|------------|---------|
| WO | 2012137019 | 10/2012 |
| WO | 2013111484 | 1/2013  |
| WO | 2013053023 | 4/2013  |
| WO | 2013064561 | 5/2013  |
| WO | 2013064562 | 5/2013  |

OTHER PUBLICATIONS

International Preliminary Report on Patentability and Written Opinion, issued by the International Searching Authority in connection with International patent application No. PCT/US2014/029138, mailed on Sep. 24, 2015, 6 pages.

Communication Pursuant to Rules 161 and 162 EPC, issued by the European Patent Office in connection with European Patent Application 14716197.0 on Oct. 23, 2015, 2 pages.

Invitation to Pay Additional Fees and, Where Applicable, Protest Fee and Communication Relating to the Results of the Partial International Search, issued by the International Searching Authority in connection with corresponding International patent application No. PCT/US2013/078041, mailed on Apr. 9, 2014, 6 pages.

International Search Report and Written Opinion, issued by the International Searching Authority in connection with corresponding International patent application No. PCT/US2014/029138, mailed on Jun. 23, 2014, 8 pages.

International Search Report and Written Opinion, issued by the International Searching Authority in connection with corresponding International patent application No. PCT/US2014/029118, mailed on Jun. 27, 2014, 9 pages.

AUTOMATED DIAGNOSTIC ANALYZERS HAVING VERTICALLY ARRANGED CAROUSELS AND RELATED METHODS

RELATED APPLICATION

This application claims the benefit under 35 U.S.C. §119 (e) to U.S. Provisional Application 61/794,060 titled "AUTOMATED DIAGNOSTIC ANALYZERS HAVING VERTICALLY ARRANGED CAROUSELS AND RELATED METHODS," filed Mar. 15, 2013, which is incorporated herein by this reference in its entirety.

FIELD OF THE DISCLOSURE

The present disclosure relates generally to automated diagnostic analyzers and, more particularly, to automated diagnostic analyzers having vertically arranged carousels and related methods.

BACKGROUND

Automated diagnostic analyzers employ multiple carousels and multiple pipetting mechanisms to automatically aspirate fluid from and dispense fluid to different areas in the analyzer to perform diagnostic analysis procedures. The carousels may include a carousel for reaction vessels, a carousel for samples and/or a carousel for reagents. By arranging multiple containers on the respective carousels, these known analyzers are capable of conducting multiple tests on multiple test samples as the carousels rotate. Some known carousels are arranged in a coplanar orientation, and a number of different modules or stations are disposed around the carousels to perform specific functions such as, for example, mixing the contents of a reaction vessel, washing a reaction vessel and/or a pipette, incubating a test sample, and analyzing the contents of a reaction vessel. Due to the multiple coplanar carousels and the number of modules and stations, these known automated clinical analyzers typically require a relatively large space.

DETAILED DESCRIPTION

Figure 1:
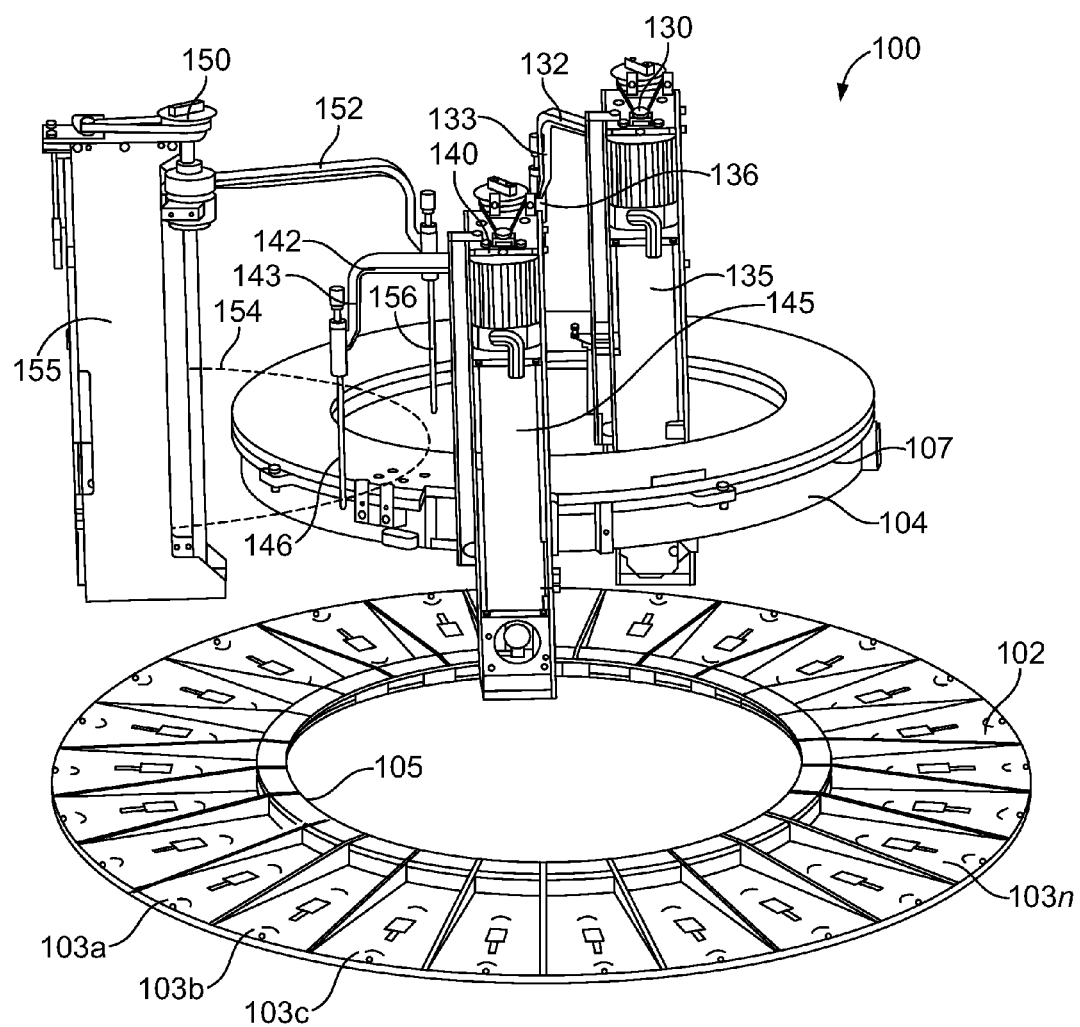
FIG. 1 is a partial exploded perspective view of example components of an example diagnostic analyzer having stacked carousels in accordance with the teachings of this disclosure.

Certain examples are shown in the above-identified figures and disclosed in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

Diagnostics laboratories employ diagnostic instruments such as those for testing and analyzing specimens or samples including, for example, clinical chemistry analyzers, immunoassay analyzers and hematology analyzers. Specimens and biological samples are analyzed to, for example, check for the presence or absence of an item of interest including, for example, a specific region of DNA, mitochondrial DNA, a specific region of RNA, messenger RNA, transfer RNA, mitochondrial RNA, a fragment, a complement, a peptide, a polypeptide, an enzyme, a prion, a protein, an antibody, an antigen, an allergen, a part of a biological entity such as a cell or a viron, a surface protein, and/or functional equivalent(s) of the above. Specimens such as a patient's body fluids (e.g., serum, whole blood, urine, swabs, plasma, cerebra-spinal fluid, lymph fluids, tissue solids) can be analyzed using a number of different tests to provide information about the patient's health.

Generally, analysis of a test sample involves the reaction of test samples with one or more reagents with respect to one or more analytes. The reaction mixtures are analyzed by an apparatus for one or more characteristics such as, for example, the presence and/or concentration of a certain analyte in the test sample. Use of automated diagnostic analyzers improves the efficiency of the laboratory procedures because the technician (e.g., an operator) has fewer tasks to perform and, thus, the potential for operator or technician error is reduced. In addition, automated diagnostic analyzers also provide results much more rapidly and with increased accuracy and repeatability.

Automated diagnostic analyzers use multiple pipettes to move liquids between storage containers (e.g., receptacles such as open topped tubes) and containers in which the specimens are to be processed (e.g., reaction vessels). For example, a specimen may be contained in a tube loaded in a rack on an analyzer, and a head carrying a pipette moves the pipette into the tube where a vacuum is applied to extract a selected amount of the specimen from the tube into the pipette. The head retracts the pipette from the tube and moves to another tube or reaction vessel located at a processing station and deposits the extracted specimen from the pipette into the reaction vessel. A reagent is similarly acquired from a reagent supply.

The example automated diagnostic analyzers disclosed herein position a first carousel (e.g., a reaction carousel, a reagent carousel, a sample carousel) above at least a portion of a second carousel (e.g., a reaction carousel, a reagent carousel, a sample carousel) to reduce lab space, increase throughput and decrease sample testing time (e.g., turnaround time). The example automated diagnostic analyzers also locate one or more pipetting mechanism(s) within the outer diameters of one of more of the carousels to further reduce the dimensions (e.g., the footprint) of the analyzer and decrease the distanced traveled by the respective pipetting mechanisms. The example automated diagnostic analyzers can simultaneously perform two or more tests on a plurality of test samples in a continuous and random access fashion. Test steps such as aspirating/dispensing, incubations, washes and specimen dilution are performed automatically by the instrument as scheduled. By utilizing vertically arranged or stacked carousels, the foot print or floor space required for the overall system is reduced. Additionally, the distanced traveled by the pipetting mechanism is also reduced, which decreases turn-around time and, thus, increases the throughput of the example analyzer. For example, in some examples, the example analyzers disclosed herein perform up to about 956 tests per hour. Further, because the carousels are stacked vertically, carousels with larger diameters and, thus, higher capacity than known analyzers may be incorporated into the example analyzers. The higher capacity analyzers occupy less space than lower capacity analyzers that have a coplanar carousel configuration. The example analyzers with smaller footprints, higher throughputs and shorter turnaround times are advantageous to the operations of hospitals, laboratories, and other research facilities that utilize diagnostic analyzers.

An example apparatus disclosed herein includes a first carousel rotatably coupled to a base and having a first diameter and a first axis of rotation. The example apparatus includes a second carousel rotatably coupled to the base and vertically spaced over the first carousel such that at least a portion of the second carousel is disposed over the first carousel. In the example apparatus, the second carousel has a second diameter, a second axis of rotation and a plurality of vessels. The example apparatus also includes a first pipetting mechanism offset from the second axis of rotation. The example first pipetting mechanism is to access the first carousel and the second carousel. In some examples, the example first pipetting mechanism is disposed within the first diameter and the second diameter and offset from the second axis of rotation.

In some examples, the first axis of rotation and the second axis are parallel to and offset from each other. In some examples, the second diameter is less than the first diameter.

In some examples, the apparatus includes a second pipetting mechanism to access the first carousel and the second carousel. In some examples, the second pipetting mechanism is disposed within the first diameter and outside of the second diameter. In some examples, the first carousel comprises an outer annular array of containers and an inner annular array of containers concentric with the outer annular array and the first pipetting mechanism is to access at least one of the inner annular array of containers or the vessels, and the second pipetting mechanism to access at least one of the outer annular array of containers or the vessels. In some examples, the first pipetting mechanism comprises a first pipette arm movable (e.g., rotatable) along a first path of travel over a first inner container of the inner annular array of containers and a first vessel of the plurality of vessels. In some such examples, the second pipette mechanism comprises a second pipette arm movable (e.g., rotatable) along a second path of travel over a second outer container of the outer annular array of containers and a second vessel of the plurality of vessels. In some examples, the second pipetting mechanism is offset from the first axis of rotation.

In some examples, the apparatus comprises a third pipetting mechanism. In some examples, the third pipetting mechanism is to access only the first carousel. In some examples, the third pipetting mechanism is disposed outside of the first diameter and outside of the second diameter. In some such examples, the third pipetting mechanism comprises a third pipette arm movable (e.g., rotatable) along a third path of travel over a container outside of the first diameter and the second diameter and over a third vessel of the plurality of vessels.

In some examples, the apparatus includes a plate coupled to the base disposed between the first carousel and the second carousel, the second carousel being rotatably coupled to the plate. In some such examples, the second pipetting mechanism is coupled to the plate.

In some examples, first carousel further comprises a middle annular array of containers spaced radially between the outer annular array of containers and the inner annular array of containers.

In some examples, the second carousel is to rotate in a plurality of intervals, each interval comprising an advancement and a stop. In some such examples, the second carousel is operable to rotate approximately 90° during the advancement of one of the intervals. In some examples, the second carousel is stationary during the stop of one of the intervals, a duration of the stop being greater than a duration of the advancement of the interval.

In some examples, the first carousel is to rotate in a plurality of intervals, each interval comprising an advancement and a stop. In some such examples, the first carousel is operable to rotate approximately 180° during the advancement of one of the intervals, a duration of the advancement being about one second of the interval.

In some examples, the apparatus includes a servo motor to rotate one or more of the first carousel or the second carousel.

In some examples, the outer annular array of containers on the first carousel contain a first type of reagent and the inner annular array of containers on the first carousel contain a second type of reagent different than the first type of reagent.

In some examples, the containers of the first carousel are reagent containers, and the vessels of the second carousel are reaction vessels. In some examples, the first pipetting mechanism comprises a probe arm having a vertically descending portion In another example disclosed herein, an apparatus includes a reagent carousel rotatably coupled to a base about a first axis of rotation. The example apparatus also includes a reaction carousel rotatably coupled to the base about a second axis of rotation, the reaction carousel disposed above the reagent carousel. In addition, the example apparatus includes a first pipette in fluid communication with the reagent carousel and the reaction carousel.

Also, in some examples disclosed herein the example apparatus includes a reagent container disposed on the reagent carousel and a reagent in the reagent container. In addition, the example apparatus includes a reaction vessel disposed on the reaction carousel. In such examples, the first pipette is to aspirate a portion of the reagent from the reagent container, move upward vertically, then dispense the portion of the reagent into the reaction vessel.

In some examples, the example apparatus also includes a second pipette to aspirate a sample from a sample container apart from the reagent carousel and the reaction carousel and dispense the sample into the reaction vessel.

An example method disclosed herein includes rotating a first carousel relative to a base, the first carousel having a first diameter, a first axis of rotation, an outer annular array of containers and an inner annular array of containers concentric with the outer annular array. The example method includes rotating a second carousel relative to the base, the second carousel having a second diameter, a second axis of rotation and a plurality of vessels and being vertically spaced over the first carousel such that at least a portion of the second carousel is disposed over the first carousel. The example method also includes aspirating a first fluid from a first carousel via a first pipetting mechanism offset from the second axis of rotation. In some examples, the first pipetting mechanism is disposed within the first diameter and within the second diameter.

In some examples, the method includes aspirating a second fluid from the first carousel via a second pipetting mechanism. In some examples, the second pipetting mechanism is disposed within the first diameter an outside of the second diameter. In some examples, the method also includes accessing at least one of the inner annular array of containers or the vessels with the first pipetting mechanism and accessing at least one of the outer annular array of containers or the vessels with the second pipetting mechanism. In some examples, the method includes rotating a first pipette arm of the first pipetting mechanism along a first path of travel over a first inner container of the inner annular array of containers and a first vessel. In some such examples, the method also includes rotating a second pipette arm of the second pipetting mechanism along a second path of travel over a first outer container of the outer annular array of containers and a second vessel. In some examples, the second pipetting mechanism is offset from the first axis of rotation.

In some examples, the method includes aspirating a third fluid via a third pipetting mechanism. In some examples, the third pipetting mechanism is disposed outside of the first diameter and outside of the second diameter. In some such examples, the method includes rotating a third pipette arm of the third pipetting mechanism along a third path of travel over a container outside of the first diameter and the second diameter and over a third vessel of the plurality of vessels.

In some examples, the method includes rotating the second carousel in a plurality of intervals, each interval comprising an advancement and a stop. In some such examples, the method includes rotating the second carousel approximately 90° during the advancement of one of the intervals. In some examples, the method includes idling the second carousel during the stop of one of the intervals, a duration of the stop being greater than a duration of an advancement of the interval.

In some examples, the method includes accessing a first vessel on the second carousel with the first pipetting mechanism, rotating the second carousel in a plurality of intervals, and rotating the second carousel for two or more intervals for the first pipetting mechanism to access a second vessel, the second vessel being physically adjacent to the first vessel.

In some examples, the method includes rotating the first carousel in a plurality of intervals, each interval comprising an advancement and a stop. In some such examples, the method includes rotating the first carousel approximately 180° during the advancement of one of the intervals, a duration of the advancement being about one second of the interval.

In some examples, the method includes activating a servo motor to rotate one or more of the first carousel or the second carousel.

Figure 2:
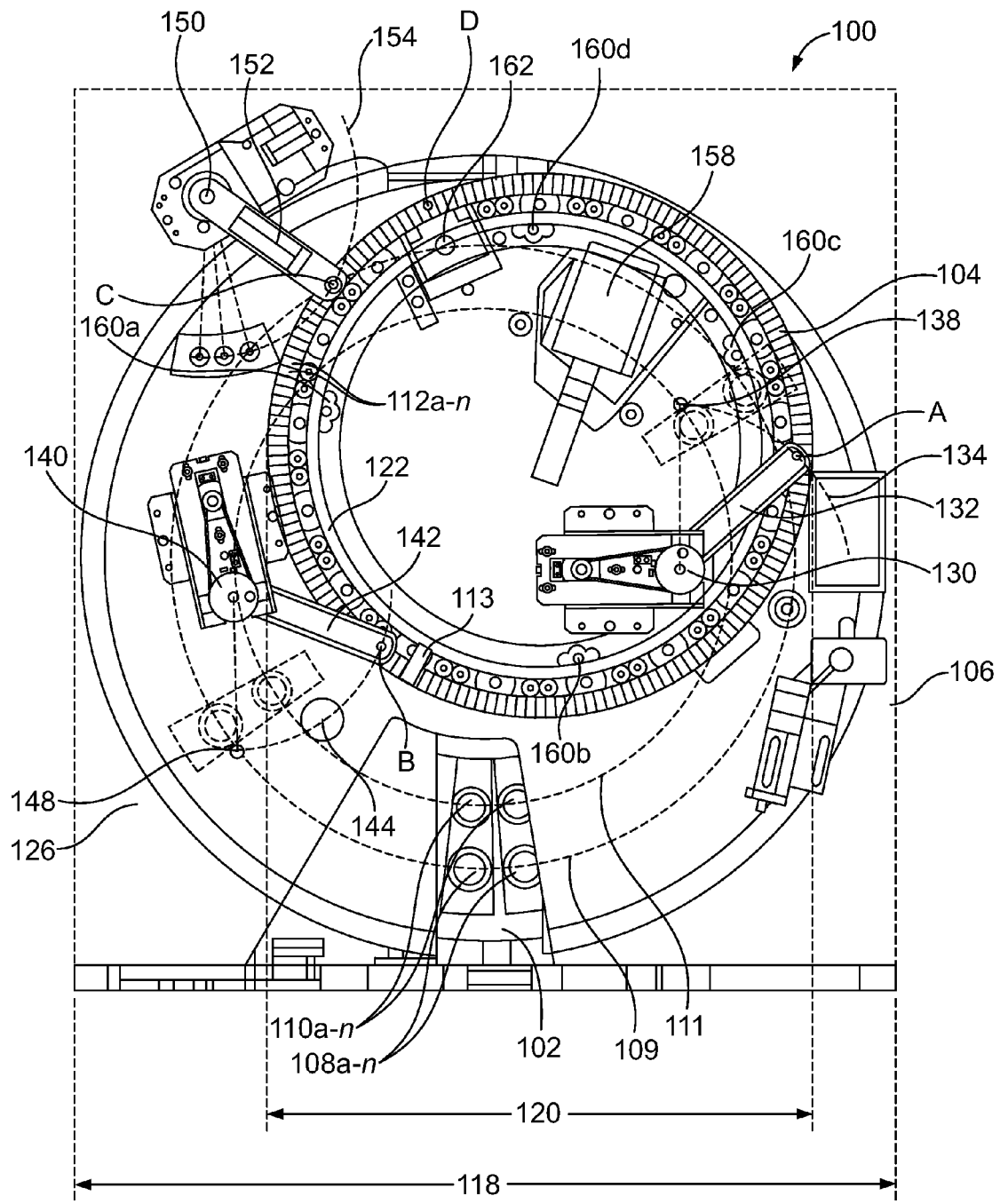
FIG. 2 shows a top view of an example diagnostic analyzer incorporating the example components of FIG. 1.
Figure 3:
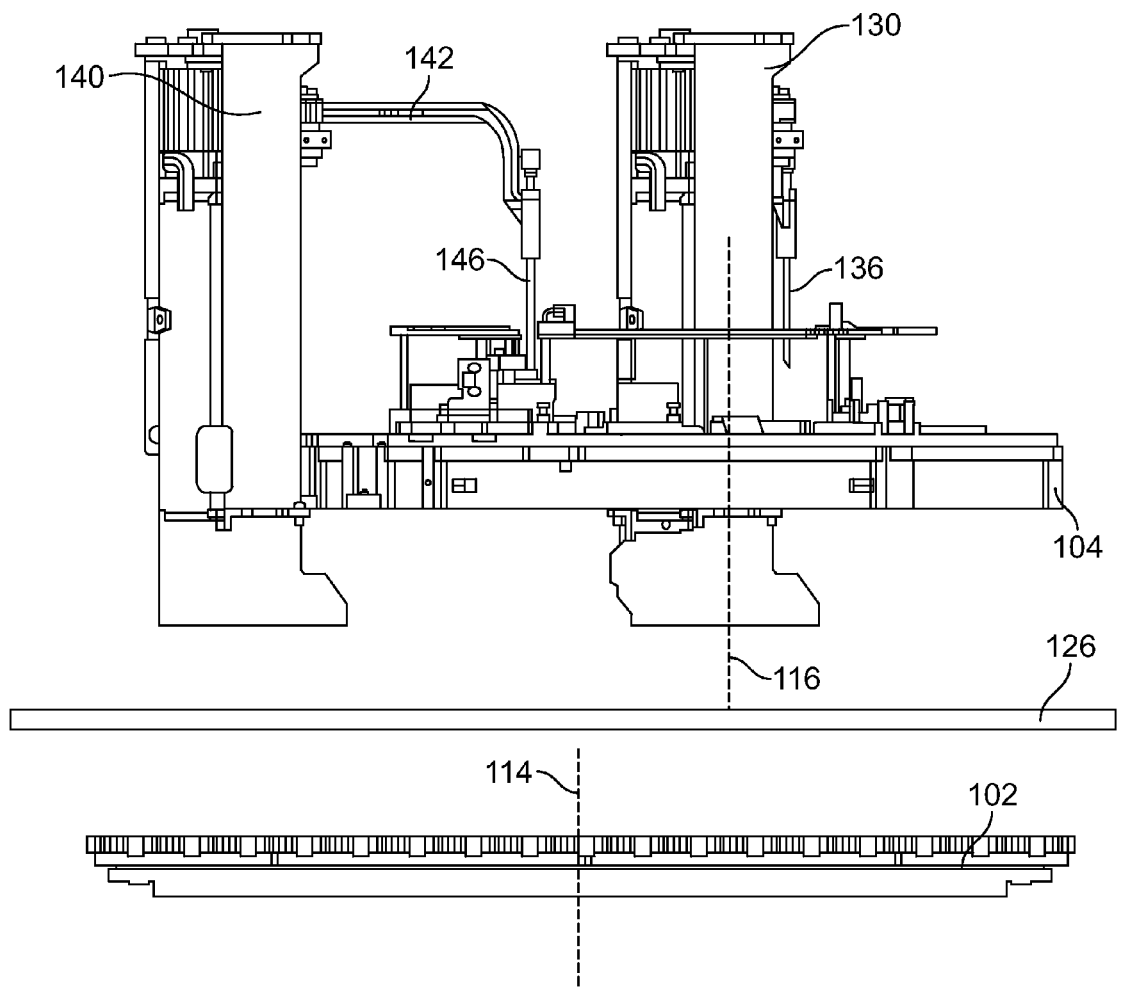
FIG. 3 is a partial exploded front side view of the example components of FIG. 1.
Figure 4:
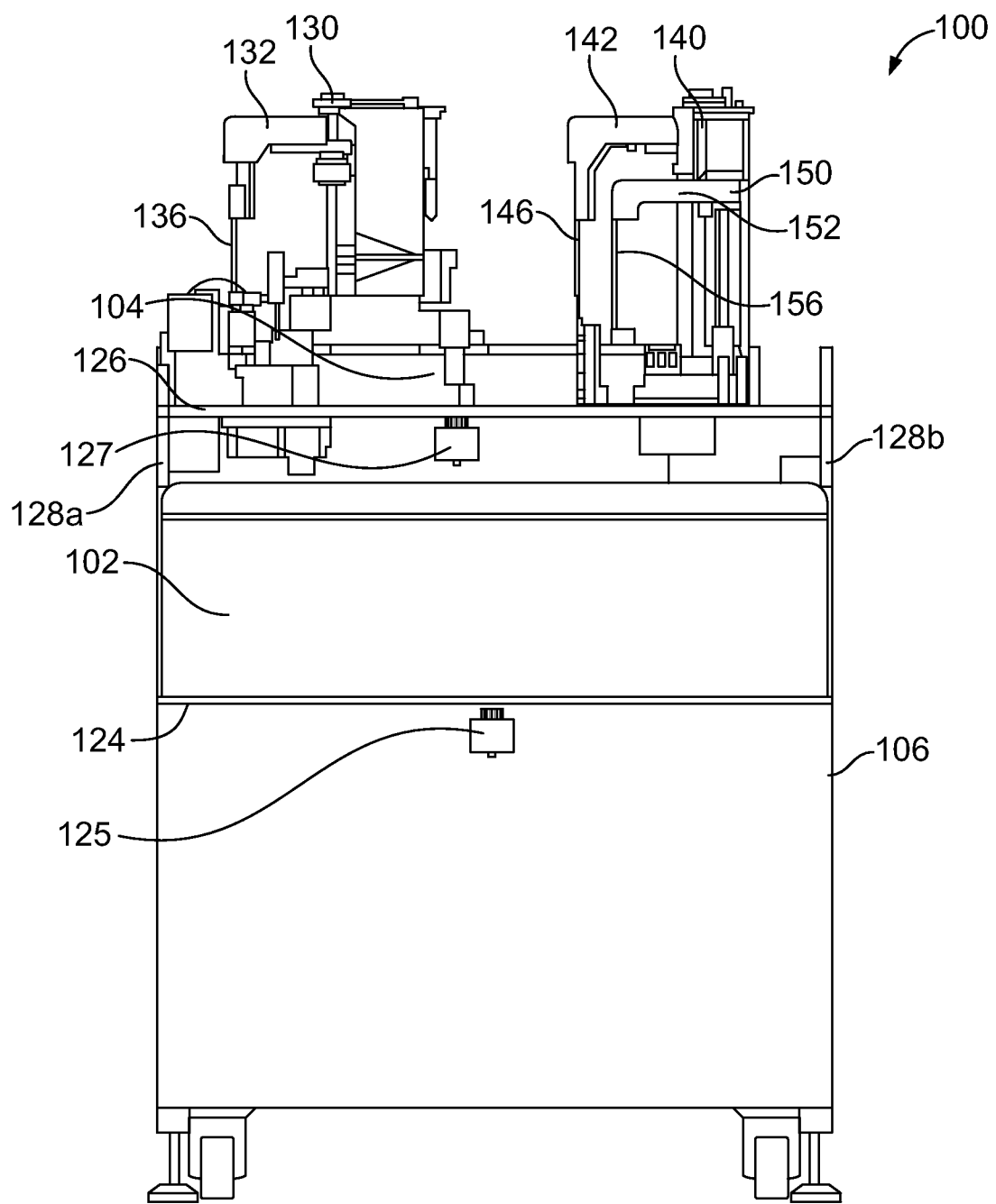
FIG. 4 shows a rear view of the example diagnostic analyzer of FIG. 2.

Turning now to the figures, a portion of an example automated diagnostic analyzer 100 is shown in partially exploded views FIGS. 1 and 3, and an assembled example analyzer 100 is shown in FIGS. 2 and 4. The example analyzer 100 includes a first carousel 102 and a second carousel 104. As shown in FIGS. 2 and 4, the first carousel 102 and the second carousel 104 are rotatably coupled to a base station 106 independent of each other. The base station 106 houses different subassemblies and other components used for testing (e.g., performing diagnostic analyses) such as, for example, wash fluid, bulk reagents, a vacuum source, a pressure source, a refrigeration system, temperature sensors, a processor, motors, etc.

In the example shown in FIGS. 1-4, the second carousel 104 is vertically spaced above the first carousel 102, and at least a portion of the second carousel 104 is disposed over (e.g., above, on top of) the first carousel 102. In the illustrated examples, the first carousel 102 is a reagent carousel and the second carousel 104 is a reaction vessel carousel. The first carousel 102 is to support multiple reagent containers that may store one or more type(s) of reagent(s). The second carousel 104 is used for conducting tests on samples. However, in other examples, either of the first and/or second carousels 102, 104 may hold reagents, samples, reaction vessels or any combination thereof.

In view of the example analyzer 100 shown in FIG. 1, the base station 106 and other components have been removed for a clear view of the first carousel 102 and the second carousel 104. In the example shown, the first carousel 102 includes a plate having a plurality of slots 103a-n. In the example shown, the first carousel 102 has a bore 105 (e.g., an opening, an aperture, a hole, etc.). In other examples the first carousel 102 may be continuous such that the first carousel 102 does not have a bore. In the example, shown, each of the slots 103a-n is to hold one or more containers or a container carrier having one or more containers. In the example shown, the second carousel 104 is housed within a casing 107. In some examples, the second carousel 104 is a reaction carousel, and some diagnostic testing utilize light signals (e.g., during chemiluminescence analysis), and readings during such testing are conducted in a dark environment to effectively read light from a reaction. Thus, in some examples, the second carousel 104 is disposed within the casing 107 to prevent light from interfering with the readings.

FIG. 2 shows a plan view of the example analyzer 100. In the example, the first carousel 102 has an outer annular array of containers 108a-n that travel along a first annular path 109 and an inner annular array of containers 110a-n that travel a second annular path 111. The outer annular array of containers 108a-n and the inner annular array of containers 110a-n are concentric. Some diagnostic tests involve one reagent and other tests utilize another, different reagent and/or two or more reagents to react with a given sample/specimen. Therefore, in some examples, the outer annular array of containers 108a-n may contain, for example, a first type of a reagent and the inner annular array of containers 110a-n may contain, for example, a second type of reagent different than the first type of reagent. Also, in some examples, the type(s) of reagent(s) within one of the annular arrays 108a-n, 110a-n may be different among the different cartridges within that array.

In some examples, the first carousel 102 has more than two annular arrays of containers (e.g., three, four or more) spaced radially apart from one another on the first carousel 102. In some examples, the containers are disposed in carriers that are loaded into the slots 103a-n of the first carousel 102. In some examples, each of the carriers may container one, two, three, four or more containers and, when disposed on the first carousel 102, define the annular arrays of containers. In some examples, the first carousel 102 includes 72 slots 103a-n to receive up to 72 carriers. In other examples, the first carousel 102 may include 45 slots 103a-n to receive up to 45 carriers. In some examples, each carrier (e.g., a kit) includes a volume of testing liquid (e.g., reagent) to supply or support about 50 to about 1700 tests. Other examples include different numbers of slots, different numbers of carriers and different volumes of testing liquids.

In the example shown, the second carousel 104 has a plurality of reaction vessels 112a-n disposed around an outer circumference of the second carousel 104. In the example shown, the reaction vessels 112a-n are reusable cuvettes (e.g., washable glass cuvettes). After a test has been completed in one of the reaction vessels 112a-n, the vessel 112a-n is cleaned (e.g., sterilized), and the vessel 112a-n may be used for another test. However, in other examples, the reaction vessels 112a-n are disposable cuvettes (e.g., plastic cuvettes) that are discarded after one or more tests. In some examples, the second carousel 104 includes an unloading mechanism 113 (e.g., a passive unloader or an active unloader) for removing the reaction vessels 112a-n (e.g., disposable cuvettes) from the second carousel 104. In some examples, the unloading mechanism 113 is positioned such that when one of the reaction vessels 112a-n is unloaded from the second carousel 104, the unloaded reaction vessel 112a-n falls through the bore 105 of the first carousel 102 and into a waste container or other receptacle disposed within the base station 106. In some examples, the second carousel 104 includes more than one unloading mechanism, and the unloading mechanisms may be disposed in other locations around the second carousel 104.

FIG. 3 illustrates a front side view of the first carousel 102 and the second carousel 104 without the base station and other components. As shown, the first carousel 102 rotates about a first axis 114 and the second carousel 104 rotates about a second axis 116. In the illustrated example, the first axis 114 and the second axis 116 are substantially parallel and offset from each other. However, in other examples, the second carousel 104 is disposed over the center of the first carousel 102 such that the first axis 114 and the second axis 116 are substantially coaxially aligned (e.g., the first carousel 102 and the second carousel 104 are concentric).

As illustrated more clearly in FIG. 2, the first carousel 102 has a first diameter 118 and the second carousel 104 has a second diameter 120. In the example shown, the second diameter 120 is less than the first diameter 118. However, in other examples, the second diameter 120 is the same as or larger than the first diameter 118. The second carousel 104 includes a bore 122 such that the second carousel forms a ring-like (e.g., annular) rack for the vessels 112a-n. As shown in this example, the second carousel 104 (e.g., the top carousel) is completely disposed above and over the first diameter 118 of the first carousel 102. In other examples, only a portion of the second diameter 120 is positioned above the first diameter 118.

In the example shown in FIG. 4, the first carousel 102 is rotatably coupled to a top 124 of the base station 106. The analyzer 100 includes a first motor 125 (e.g., a stepper motor or a servo motor) to rotate the first carousel 102 on the top 124 of base station 106. In the example shown, the analyzer 100 also includes a platform 126 (e.g., a plate, a mounting surface, a shield) mounted to the base station 106 via a plurality of legs 128a, 128b and disposed between the first carousel 102 and the second carousel 104. In other examples, the platform 126 may be mounted to the base station 106 with other fasteners. The platform 126 defines a partition or barrier between the first carousel 102 and the second carousel 104. In the example shown, the second carousel 104 is rotatably mounted to the platform 126. However, in other examples, the second carousel 104 may be rotatably supported on the base station 106 without the mounting platform 126. The second carousel 104 is rotated via a second motor 127 (e.g., a stepper motor or a servo motor). In the example shown, the first and second carousels 102, 104 may be rotated clockwise and/or counterclockwise, depending on the scheduling protocols for the particular testing.

The example automated diagnostic analyzers disclosed herein also include one or more pipetting mechanisms (e.g., probe arms, automated pipettes, etc.). In the illustrated examples shown in FIGS. 1-4, the analyzer 100 includes a first pipetting mechanism 130 that is coupled (e.g., mounted) to the platform 126. The first pipetting mechanism 130 is coupled to the platform 126 above the first carousel 102 and within the bore 122 of the second carousel 104 (i.e., within the first diameter 118 of the first carousel 102 and within the second diameter 120 of the second carousel 104). In the example shown, the first pipetting mechanism 130 is offset from the second axis 116 (e.g., the center of the second carousel 104). However, in other examples the first pipetting mechanism 130 is aligned with the second axis 116. The first pipetting mechanism 130 has multiple degrees of freedom. In the example shown, the first pipetting mechanism 130 has a first probe arm 132 that moves in a first path of travel (e.g., along a horizontal arc) 134 and aspirates/dispenses fluid through a first pipette 136 located at a distal end of the first probe arm 132. The first pipetting mechanism 130 is also movable in the Z direction (e.g., the vertical direction).

As illustrated in FIG. 2, the first pipetting mechanism 130 accesses containers on the first carousel 102 through a first access port 138, which may be for example, an opening, an aperture, a hole, a gap, etc. formed in the platform 126. In operation, the first pipetting mechanism 130 moves the first probe arm 132 along the first path of travel 134 (e.g., rotates or pivots clockwise) until the first pipette 136 is aligned above the first access port 138. The first path of travel 134 may be circular, semicircular, linear or a combination thereof. The first pipetting mechanism 130 then moves vertically downward until the first pipette 136 accesses a container on the first carousel 102 to aspirate/dispense liquid (including, for example, microparticles contained in the liquid) from the container. In the example shown, the first pipetting mechanism 130 and the first access port 138 are positioned to allow the first pipetting mechanism 130 to aspirate from a container disposed on the first carousel 102 below the first access port 138. The first carousel 102 holds the outer annular array of containers 108a-n and the inner annular array of containers 110a-n, which may be, for example, first reagents used in a diagnostic test and second reagents used in the diagnostic test, respectively. In the illustrated example, the first pipetting mechanism 130 is positioned (e.g., aligned) to aspirate fluid from a container of the inner annular array of containers 110a-n on the first carousel 102. As shown, the inner annular array of containers 110a-n rotate along the second annular path 111, which intersects with the first access port 138 and, thus, the second path of travel 134. In the example shown, a silhouette of a carrier, having two containers (e.g., an outer annular container and an inner annular container), is depicted near the first access port 138 to illustrate the interaction of the containers, the first access port 138 and/or the first path of travel 134.

After aspirating fluid from the appropriate container on the first carousel 102, the first pipetting mechanism 130 moves vertically upward and moves the first probe arm 132 along the first path of travel 134 (e.g., rotates or pivots clockwise) until the first pipette 136 is at point A, at which point the first pipette 136 is aligned vertically over one of the plurality of vessels 112a-n on the second carousel 104. In some examples, the first pipetting mechanism 130 dispenses the liquid (e.g., the liquid including any microparticles aspirated from a container on the first carousel 102) into the vessel 112a-n on the second carousel 104 at this position (e.g., the height at which the first pipette 136 travels along the first path of travel 134). In other examples, the first pipetting mechanism 130 moves vertically downward toward the second carousel 104 and dispenses the liquid into the vessel 112a-n on the second carousel 104. In the illustrated example, the first pipetting mechanism 130 has only one access point, the first access port 138, for accessing containers on the first carousel 102 disposed below. However, in other examples, the platform 126 includes multiple access ports along the first path of travel 134 such that the first pipette 136 can access additional areas on the first carousel 102. In some examples, multiple annular arrays of containers (e.g., an inner array and an outer array or an inner array, a middle array and an outer array) are disposed on the first carousel 102 at different radial distances (e.g., along the slots 103 shown in FIG. 1) and, thus, multiple access points along the first path of travel 134 allow the first pipetting mechanism 130 to access these containers as needed and/or desired.

In the example shown, the analyzer 100 includes a second pipetting mechanism 140 that is coupled (e.g., mounted) to the platform 126. The second pipetting mechanism 140 is coupled to the platform 126 above the first carousel 102 and next to (e.g., adjacent) the second carousel 104 (i.e., within the first diameter 118 of the first carousel 102 and outside of the second diameter 120 of the second carousel 104). In the example shown, the second pipetting mechanism 140 is offset from the first axis 114 of the first carousel 102. However, in other examples, the second pipetting mechanism 140 is aligned with the first axis 114 of rotation. The second pipetting mechanism 140 has multiple degrees of freedom. In the example shown, the second pipetting mechanism 140 has a second probe arm 142 that moves along a second path of travel 144 (e.g., rotates or pivots along a horizontal arc) to aspirate/dispense fluid through a second pipette 146 disposed at a distal end of the second probe arm 142. The second path of travel 144 may be circular, semicircular, linear or a combination thereof. The second pipetting mechanism 140 is also movable in the Z direction (e.g., the vertical direction).

In the example shown, the second pipetting mechanism 140 accesses containers on the first carousel 102 through a second access port 148 formed in the platform 126. In operation, the second pipetting mechanism 140 moves (e.g., rotates or pivots) the second probe arm 142 along the second path of travel 144 until the second pipette 146 is aligned above the second access port 148. The second pipetting mechanism 140 then moves vertically downward for the second pipette 146 to access a container on the first carousel 102. In the example shown, the second pipetting mechanism 140 and the second access port 148 are positioned to allow the second pipetting mechanism to aspirate from a container disposed on the first carousel 102 below the second access port 148. As mentioned above, the first carousel 102 includes the outer annular array of containers 108a-n and the inner annular array of containers 110a-n, which may be, for example, reagents used first in a diagnostic test and reagents used second in the diagnostic test. In the illustrated example, the second pipetting mechanism 140 is positioned (e.g., aligned) to aspirate liquid including any microparticles from the outer annular array of containers 108a-n on the first carousel 102. As shown, the outer annular array of containers 108a-n rotate along the first annular path 109, which intersects with the second access port 148 and, thus, the second path of travel 144. In the example shown, a silhouette of a carrier, having two containers (e.g., an outer annular container and an inner annular container), is depicted near the second access port 148 to illustrate the interaction of the containers, the second access port 148 and/or the second path of travel 144.

After aspirating liquid and any associated microparticles from the appropriate container on the first carousel 102, the second pipetting mechanism 140 moves vertically upward and moves (e.g., rotates or pivots) the second probe arm 142 counter-clockwise along the second path of travel 144 until the second pipette 146 is at point B, at which point the second pipette 146 is aligned vertically over one of the plurality of vessels 112a-n on the second carousel 104. In some examples, the second pipetting mechanism 140 dispenses the liquid (e.g., the liquid including any microparticles aspirated from a container on the first carousel 102) into the vessel 112a-n on the second carousel 104 at this position (e.g., the height at which the second pipette 146 travels along the second path of travel 144). In other examples, the second pipetting mechanism 140 moves vertically downward toward the second carousel 104 and dispenses the liquid into the vessel 112a-n on the second carousel 104. In the illustrated example, the second pipetting mechanism 140 has one access point, the second access port 148, for accessing containers on the second carousel 104 disposed below. However, in other examples, the platform 126 includes multiple access ports along the second path of travel 144 such that the second pipette 146 can access additional areas on the first carousel 102. In some examples, multiple annular arrays of containers (e.g., an inner array and an outer array or an inner array, a middle array and an outer array) are disposed on the first carousel 102 at different radial distances and, thus, multiple access points along the second path of travel 144 will allow the second pipetting mechanism 140 to access the containers as needed.

In the illustrated examples, the analyzer 100 includes a third pipetting mechanism 150. In the example shown, the third pipetting mechanism 150 is coupled to the platform 126. In other examples, the third pipetting mechanism 150 may be coupled to the top 124 of the base station 106. In the example shown, the third pipetting mechanism 150 is disposed outside of the first diameter 118 of the first carousel 102 and outside of the second diameter 120 of the second carousel 104. However, in other examples, the third pipetting mechanism 150 is disposed within the first diameter 118 of the first carousel 102. In the example shown, the third pipetting mechanism 150 is mounted at a level above the first carousel 102. Specifically, the third pipetting mechanism 150 is mounted to the platform 126 above the first carousel 102.

The third pipetting mechanism 150 has multiple degrees of freedom. In the example shown, the third pipetting mechanism 150 has a third probe arm 152 that rotates along a third path of travel 154 (e.g., a horizontal arc) to aspirate/dispense liquid (e.g., a sample) through a third pipette 156 at a distal end of the third probe arm 152. The third path of travel 154 may be circular, semicircular, linear or a combination thereof. The third pipetting mechanism 150 is also movable in the Z direction (e.g., the vertical direction).

In the example shown, the third pipetting mechanism 150 may be used, for example, to dispense a sample (e.g., a test sample or a specimen) into one or more of the vessels 112a-n on the second carousel 104. In some examples, test samples are aspirated from sample containers (which may be in carriers) along the third path of travel 154 of the third pipetting mechanism 150. In some examples, test samples are transported to the rear of the analyzer 100 via a transporter or a positioner, and the third probe arm 152 moves (e.g., rotates or pivots) along the third path of travel 154 to align the third pipetting mechanism 150 above the sample tubes. After aspirating a sample from a sample tube, the third pipetting mechanism 150 moves (e.g., rotates or pivots) the third probe arm 152 along the third path of travel 154 until the third pipette 156 is at point C, where the third pipette 156 is vertically aligned above one of the reaction vessels 112a-n on the second carousel 104. The third pipetting mechanism 150 moves vertically downward toward the second carousel 104 and dispenses the sample into one of the vessels 112a-n on the second carousel 104.

In the example shown, three pipetting mechanisms 130, 140, 150 are employed to perform automated testing. However, in other example analyzers, more or fewer automated pipetting mechanisms may be utilized (such as, for example, one, two, four, five, etc.). For example, there may be a fourth pipetting mechanism, which also may be used to dispense samples into one of the vessels 112*a-n* on the second carousel 104. Also, in some examples, one or more of the pipetting mechanisms may include a double probe to enable the pipetting mechanism to aspirate from and/or dispense to two containers and/or vessels simultaneously. For example, with two probes on the third pipetting mechanism 150, the third pipetting mechanism 150 can dispense a first sample in a first vessel and a second sample in a second vessel. In addition, in some examples, the pipetting mechanisms may be located in different locations, to perform the steps for analysis. Further, in some example analyzers, the pipetting mechanisms 130, 140, 150 may aspirate from multiple sources and dispense into multiple locations (e.g., containers and vessels) along their respective paths of travel.

In the example analyzer 100 shown in FIGS. 1-4, the first and second pipetting mechanisms 130, 140 have a larger Z direction range (e.g., a vertical range or stroke) than pipetting mechanisms in known analyzers, because the first and second pipetting mechanisms 130, 140 is to access the containers 108*a-n*, 110*a-n* on the first carousel 102 at a lower level and the vessels 112*a-n* on the second carousel 104 at a higher level. Thus, in some examples, the height (e.g., the vertical position of the tip of the pipette 136, 146) at which the pipettes 136, 146 aspirate liquid from the containers 108*a-n*, 110*a-n* on the first carousel 102 is different than the height at which the pipettes 136, 146 dispense liquid into the vessels 112*a-n*. The example pipette 136, 146 tips are positioned at a first height to access the containers 108*a-n*, 110*a-n* on the first carousel 102 and a second height to access the vessels 112*a-n* on the first carousel 102, the first height being lower (e.g., closer to the base 106) than the second height. In some examples, each of the probe arms 132, 142 includes a downward or vertically descending portion 133, 143 to allow the pipetting mechanisms 130, 140 to incorporate a standard sized pipette or probe. In such examples, the downward portion 133, 143 of the probe arms 132, 142 displaces the pipettes or probes further from the probe arms 132, 142 to ensure the pipettes have access into the containers 108*a-n*, 110*a-n* on the first carousel 102. With the downward portions 133, 143, the pipettes are able to access the bottom of the containers 108*a-n*, 110*a-n* on the first carousel 102 without, for example, the platform 126 blocking a downward or vertical descent of the probe arms 132, 142. Use of a standard size pipette or probe, as compared to a longer pipette or probe, reduces the effects of vibrations (e.g., from the motors, mixers, etc.) on the pipette or probe, resulting in greater operation accuracy.

In some examples, the length of the probe arms 132, 142, 152 and/or the length of the paths of travel 134, 144, 154 are shorter than the probe arms of some known analyzers. The decreased probe arm length of the illustrated examples reduces the effects of vibrations (e.g., from the motors, mixers, etc.) on the pipetting mechanisms 130, 140, 150 because the respective pipettes 136, 146, 156 are closer to the base of the respective pipetting mechanisms 130, 140, 150 and, thus, are closer to the center of mass and are sturdier. The sturdier probes arms 132, 142, 152 enable the example pipetting mechanisms 130, 140, 150 to operate with greater accuracy. The example pipetting mechanisms 130, 140, 150 may also operate with greater speed because there is no need to wait for vibrations to dampen or otherwise subside before operation of the pipetting mechanisms 130, 140, 150. In the example shown, the first, second and third pipetting mechanisms 130, 140, 150 include respective base assemblies 135, 145, 155. In some examples, the base assemblies 135, 145, 155 include drive components and other actuating components to move the first, second and third probe arms 132, 142, 152 in the Z direction.

Although the first and second carousels 102, 104 are disclosed herein as being a reagent carousel and a reaction carousel, respectively, the teachings of this disclosure may be applied to examples in which either the first carousel 102 and/or the second carousel 104 includes reagents, reaction vessels and/or samples. Thus, the first carousel 102 may be a reaction carousel including a plurality of reaction vessels, and the second carousel 104 may be a reagent carousel including a plurality of reagent containers having reagent(s) for reacting with the samples in the reaction vessels.

In the example shown, the analyzer 100 also includes additional modules or components for performing different steps in the test process such as, for example, a mixer for mixing, a light source for lighting the reaction vessels, a reader for analyzing the test samples, a wash zone for cleaning the vessels, etc. As shown in FIG. 2, the example analyzer 100 includes a reader 158, a plurality of mixers 160*a-d*, and a wash station 162 for cleaning the reaction vessels. In some examples, the reaction vessels 112*a-n* are cleaned at the wash station 162 at point D. In some examples, the mixers 160*a-d* (e.g., in-track vortexers (ITV)) are coupled to the platform 126 disposed between the first carousel 102 and the second carousel 104, which may, for example, dampen the vibrating effects of the mixers 160*a-d* and reduce the influence they have on the pipetting mechanisms 130, 140, 150 and other components of the analyzer 100. In some examples, the mixers 160*a-d* are disposed beneath the vessels 112*a-n* on the second carousel 104. In some examples, the analyzer 100 includes one or more wash zones coupled to the platform 126 and disposed along the first, second and/or third paths of travel 134, 144, 154. In some examples, the pipettes 136, 146, 156 are cleaned between aspirating/dispensing functions in the wash zones.

In the example shown, the first and second carousels 102, 104 rotate in intervals or locksteps during a diagnostic test. Each interval has an advancement step wherein the carousel moves and stop step where the carousel is idle. Depending on the type of diagnostic test performed, the carousels 102, 104 may have different lockstep times and rotational degrees that are traversed during the advancement step. In the example shown, the second carousel 104 has total a lockstep time (the combination of an advancement step and a stop step) of about four seconds (i.e., the second carousel 104 rotates incrementally to a different position about every four seconds). During the advancement step of the lockstep, the second carousel 104 rotates about 90° (e.g., about a quarter turn). In other examples, the second carousel 104 may rotate more or less depending on the scheduling protocols designed for the specific analyzer and/or for a particular diagnostic testing protocol. In some examples, the second carousel 104 rotates about 1° to about 15° during the advancement step of the lockstep. In other examples, the second carousel rotates about 15° to about 90° during the advancement step of the lockstep.

In the example shown, the advancement step may take place during about one second of the four second lockstep, and the second carousel 104 may remain idle (e.g., stationary) for about three second during the stop step of the lockstep. During these three seconds, the first, second and third pipetting mechanisms 130, 140, 150 are aspirating and/or dispensing liquids (e.g., simultaneously or in sequence), including any microparticles contained therein, and other functional modules are operating around the carousels 102, 104. Some of the functional modules such as, for example, the reader 158, also operate during the advancement step of a lockstep. Additionally or alternatively, the reader 158 operates during the stop step of a lockstep.

In some examples, the first carousel 102 has a lockstep time of about two seconds. For each lockstep, the first carousel 102 rotates during one second (e.g., an advancement step) and is idle (e.g., stationary) for one second (e.g., a stop step). The lockstep time for the first carousel 102 is half of the lockstep time for the second carousel 104 so that the first carousel 102 may be repositioned during one lockstep of the second carousel 104, and a second reagent can be aspirated from the first carousel 102 and dispensed into the second carousel 104 during one lockstep of second carousel 104. For example, a first reagent container on the outer annular array of containers 108a-n and a second reagent container on the inner annular array of container 110a-n may be on the same radial slot 103a-n on the first carousel 102. In this example, if both reagents are to be used during a single lockstep of the second carousel 104, during the first lockstep for the first carousel 102, the second pipetting mechanism 140 may aspirate a reagent from the outer annular array of containers 108a-n. After the second pipette 146 has left the container, the first carousel 102 rotates to its second lockstep position so that the first pipetting mechanism 130 can aspirate its desired reagent from the inner annular array of container 110a-n during the same lockstep of the second carousel 104. In some examples, depending on the location of the pipetting mechanisms, the first carousel 102 is rotated approximately 180° to the next position so the next pipetting mechanism can aspirate and dispense in accordance with the testing protocol. Thus, both the first and second pipetting mechanisms 130, 140 can aspirate from containers in any of the slots 103a-n of the first carousel 102 in one lockstep of the second carousel 104. In addition, in some examples, the first and second pipetting mechanisms 130, 140 may interact with the first carousel 102 during the stop step portion of the lockstep of the first carousel 102 while the second carousel 104 rotates in the advancement step of the lockstep of the second carousel 104.

Figure 5:
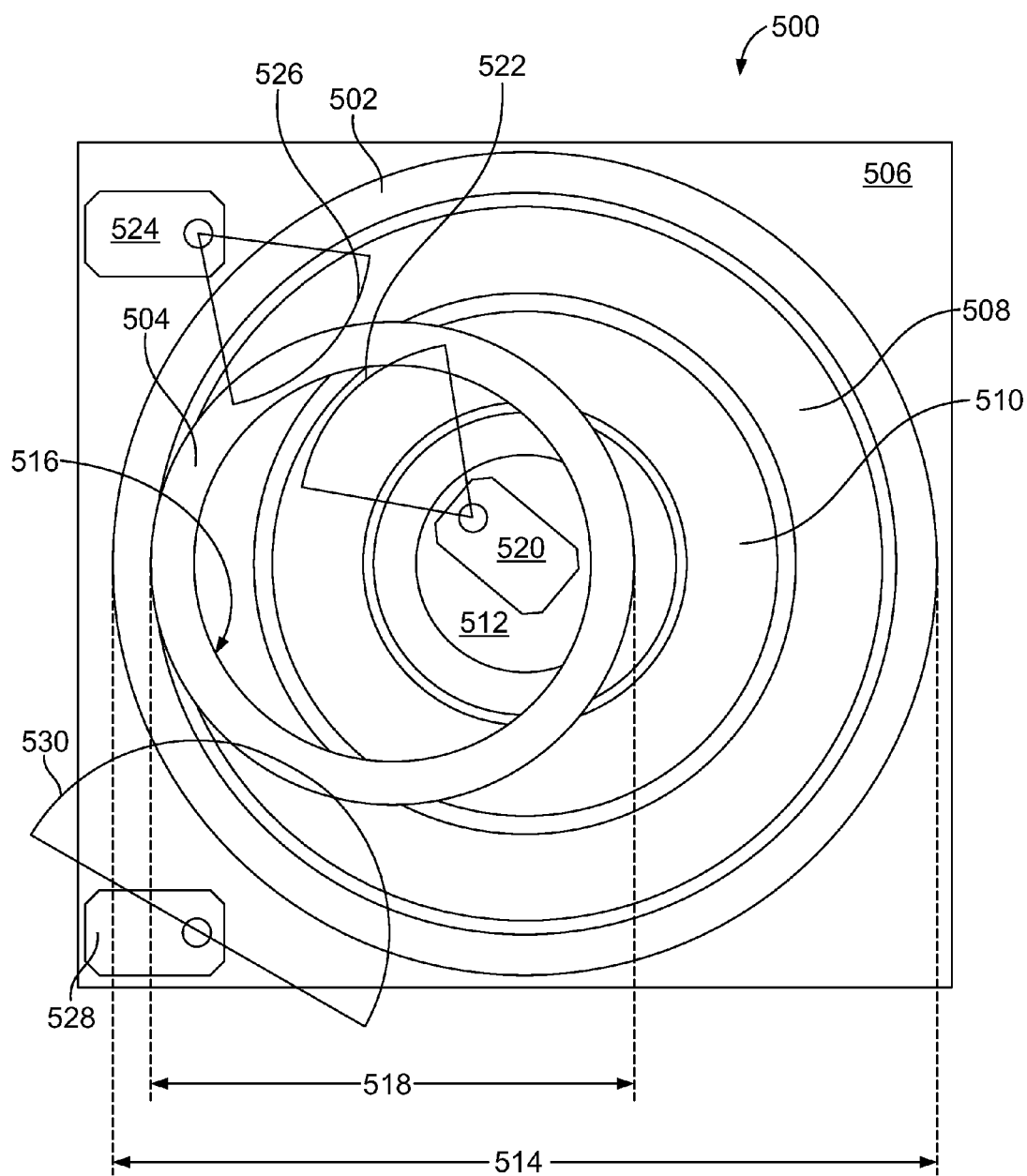
FIG. 5 is a schematic a plan view of an example diagnostic analyzer with an alternative carousel configuration.

FIG. 5 illustrates an example analyzer 500 with an alternative configuration of carousels and pipetting mechanisms. In this example, the analyzer 500 includes a first carousel 502 and a second carousel 504 that are each rotatably coupled to a base 506. The second carousel 504 is disposed above and over the first carousel 502. The first carousel 502 may be, for example, a reagent carousel having a plurality of reagent containers and the second carousel 504 may be, for example, a reaction carousel having a plurality of reaction vessels.

In the example shown, the first carousel 502 has an outer annular section 508 for containers and an inner annular section 510 for containers. In some examples, containers on the outer annular section 508 may be, for example, reagent containers that hold a first reagent to be used in a first step in a test process, and containers on the inner annular section 510 may be, for example, reagent containers that hold a second reagent to be used either in a second step in the test process and/or in a second test process different than the first.

As shown, the first carousel 502 has a first bore 512 and a first diameter 514, and the second carousel 504 has a second bore 516 and a second diameter 518. In this example, a center of the second carousel 504 is offset from a center of the first carousel 502 and within the first diameter 516 (i.e., the second carousel 504 is disposed vertically above the first carousel 502 and positioned within the outer bounds of the first carousel 502).

The analyzer 500 includes a first pipetting mechanism 520 disposed within the first diameter 514 of the first carousel 502 and within the second diameter 518 of the second carousel 504. In the example shown, the first pipetting mechanism 520 is also disposed within the first bore 512 of the first carousel 502 and the second bore 516 of the second carousel 504. In some examples, the first pipetting mechanism 520 is mounted to the base 506. In other examples, the first pipetting mechanism 520 is mounted to a platform disposed between the first carousel 502 and the second carousel 504. In the example shown, the first pipetting mechanism 520 moves in the Z direction (e.g., vertically) and rotates or otherwise moves to aspirate/dispense liquid including liquids that have microparticles within a first probe arm radius or range of motion 522. The first probe arm radius 522 is capable of extending over a portion of the inner annular section 510 of the first carousel 502 and over a portion of the second carousel 504 such that the first pipetting mechanism 520 is able to aspirate/dispense from/to containers or vessels disposed on the inner annular section 510 of the first carousel 502 and/or containers or vessels on disposed on the second carousel 504. Thus, the first pipetting mechanism 520 may be used, for example, to aspirate a reagent from a container on the first carousel 502 and dispense the reagent into a reaction vessel on the second carousel 504.

The analyzer 500 includes a second pipetting mechanism 524 disposed outside the first diameter 514 of the first carousel 502 and outside of the second diameter 518 of the second carousel 504. In some examples, the second pipetting mechanism 524 is mounted to the base 506. In other examples, the second pipetting mechanism is mounted to a platform disposed between the first carousel 502 and the second carousel 504. The second pipetting mechanism 524 moves in the Z direction (e.g., vertically) and rotates or otherwise moves to aspirate/dispense fluid within a second probe arm radius or range of motion 526. As shown, the second probe arm radius 526 extends over a portion of the outer annular section 508 of the first carousel 502 and a portion of the second carousel 504 such that the second pipetting mechanism 524 is able to aspirate/dispense from/to containers or vessels disposed on the outer annular section 508 of the first carousel 502 and/or containers or vessels on disposed on the second carousel 504. Thus, the second pipetting mechanism 524 may be used, for example, to aspirate a reagent from a container on the first carousel 502 and dispense the reagent into a reaction vessel on the second carousel 504.

The example analyzer 500 includes a third pipetting mechanism 528 disposed outside the first diameter 514 of the first carousel 502 and outside of the second diameter 518 of the second carousel 504. In some examples, the third pipetting mechanism 528 is mounted to the base 506. In other examples, the third pipetting mechanism 528 is mounted to a platform disposed between the first carousel 502 and the second carousel 504. The third pipetting mechanism 528 moves in the Z direction (e.g., vertically) and rotates or otherwise moved to aspirate/dispense fluid within a third probe arm radius 530. As shown, the third probe arm radius or range of motion 530 extends over a portion of the outer annular section 508 of the first carousel 502, a portion of the second carousel 504, and a region outside of the base 506 of the analyzer 500. The third pipetting mechanism 528 may be used, for example, to aspirate sample from a test sample tube disposed outside of the base 506 (e.g., from another portion of the analyzer 500) and to dispense the sample into a container or vessel on the second carousel 504.

In the example shown, the inner annular section 510 and the outer annular section 508 are formed in the same carousel 502 and, thus, rotate together. However, in other examples, the inner annular section 510 and the outer annular section 508 may be separate carousels that are independently rotatable in either direction.

As shown, the first, second and third pipetting mechanisms 520, 524, 528 are disposed within the first and second diameters 514, 518 and/or in the corners of the base 506. In addition, the first carousel 502 and second carousel 504 are stacked. Thus, the footprint of the example analyzer 500 is less than an analyzer with coplanar carousels.

Figure 6:
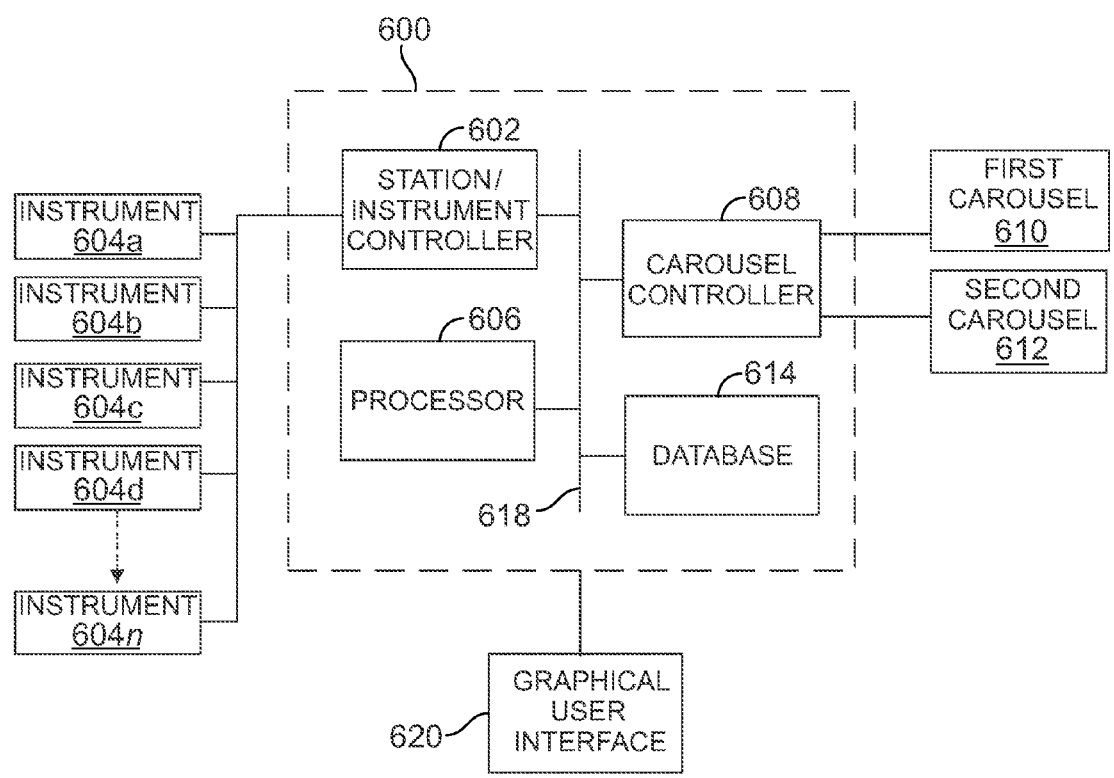
FIG. 6 is a block diagram of an example processing system for the example analyzers shown in FIGS. 1-5.

FIG. 6 is a block diagram of an example processing system 600 for use with an automated diagnostic analyzer such as, for example, the analyzers 100, 500 disclosed above. The example processing system 600 includes a station/instrument controller 602, which controls the instruments and mechanisms used during a diagnostic test. In the example shown, the station/instrument controller 602 is communicatively coupled to instruments 604a-n. The instruments 604a-n may include, for example, components of the example analyzer 100 disclosed above including the first pipetting mechanism 130, the second pipetting mechanism 140, the third pipetting mechanism 150, the ITVs 160a-d, the wash zone 162 and/or the reader 158. The example processing system 600 includes an example processor 606 that operates the station/instrument controller 602 and, thus, the instruments 604a-n in accordance with a schedule or testing protocol as disclosed herein.

The example processing system 600 also includes a carousel controller 608, which controls one or more carousels of the analyzer. In the example shown, the carousel controller 608 is communicatively coupled to a first carousel 610 and a second carousel 612. The first carousel 610 and the second carousel 612 may correspond, for example, to the first and second carousels 102, 104 disclosed above in connection with the example analyzer 100. The carousel controller 608 controls the rotation of the first and second carousels 610, 612, such as, for example, using a motor (e.g., the motors 125, 127 disclosed in connection with the analyzer 100). Also, the example processor 606 operates the carousel controller 608 and, thus, the carousels 610, 612 in accordance with a schedule or testing protocol.

The example processing system 600 also includes a database 614 that may store information related to the operation of the example system 600. The information may include, for example, the testing protocol, reagent identification information, reagent volume information, sample identification information, position information related to a position (e.g., reaction vessel, lockstep and/or rotation) of a sample, status information related to the contents and/or position of a reaction vessel, pipette position information, carousel position information, lockstep duration information, etc.

The example processing system 600 also includes a user interface such as, for example, a graphical user interface (GUI) 616. An operator or technician interacts with the processing system 600 and, thus, the analyzer 100, 500 via the interface 616 to provide, for example, commands related to the testing protocols, information related to the samples to be tested, information related to the reagents or other fluids to be used in the testing, etc. The interface 616 may also be used by the operator to obtain information related to the status and/or results of any testing completed and/or in progress.

In the example shown, the processing system components 602, 606, 608, 614 are communicatively coupled to other components of the example system 600 via communication links 618. The communication links 618 may be any type of wired connection (e.g., a databus, a USB connection, etc.) and/or any type of wireless communication (e.g., radio frequency, infrared, etc.) using any past, present or future communication protocol (e.g., Bluetooth, USB 2.0, USB 3.0, etc.). Also, the components of the example system 600 may be integrated in one device or distributed over two or more devices.

While an example manner of implementing the analyzers 100, 500 of FIGS. 1-5 is illustrated in FIG. 6, one or more of the elements, processes and/or devices illustrated in FIG. 6 may be combined, divided, re-arranged, omitted, eliminated and/or implemented in any other way. Further, the example station/instrument controller 602, the example instruments 604a-n, the example processor 606, the example carousel controller 608, the example first carousel 610, the example second carousel 612, the example database 614, the example graphical user interface 616 and/or, more generally, the example processing system 600 of FIG. 6 may be implemented by hardware, software, firmware and/or any combination of hardware, software and/or firmware. Thus, for example, any of the example station/instrument controller 602, the example instruments 604a-n, the example processor 606, the example carousel controller 608, the example first carousel 610, the example second carousel 612, the example database 614, the example graphical user interface 616 and/or, more generally, the example processing system 600 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example station/instrument controller 602, the example instruments 604a-n, the example processor 606, the example carousel controller 608, the example first carousel 610, the example second carousel 612, the example database 614 and/or the example graphical user interface 616 is/are hereby expressly defined to include a tangible computer readable storage device or storage disk such as a memory, a digital versatile disk (DVD), a compact disk (CD), a Blu-ray disk, etc. storing the software and/or firmware. Further still, the example processing system 600 of FIG. 6 may include one or more elements, processes and/or devices in addition to, or instead of, those illustrated in FIG. 6, and/or may include more than one of any or all of the illustrated elements, processes and devices.

Figure 7:
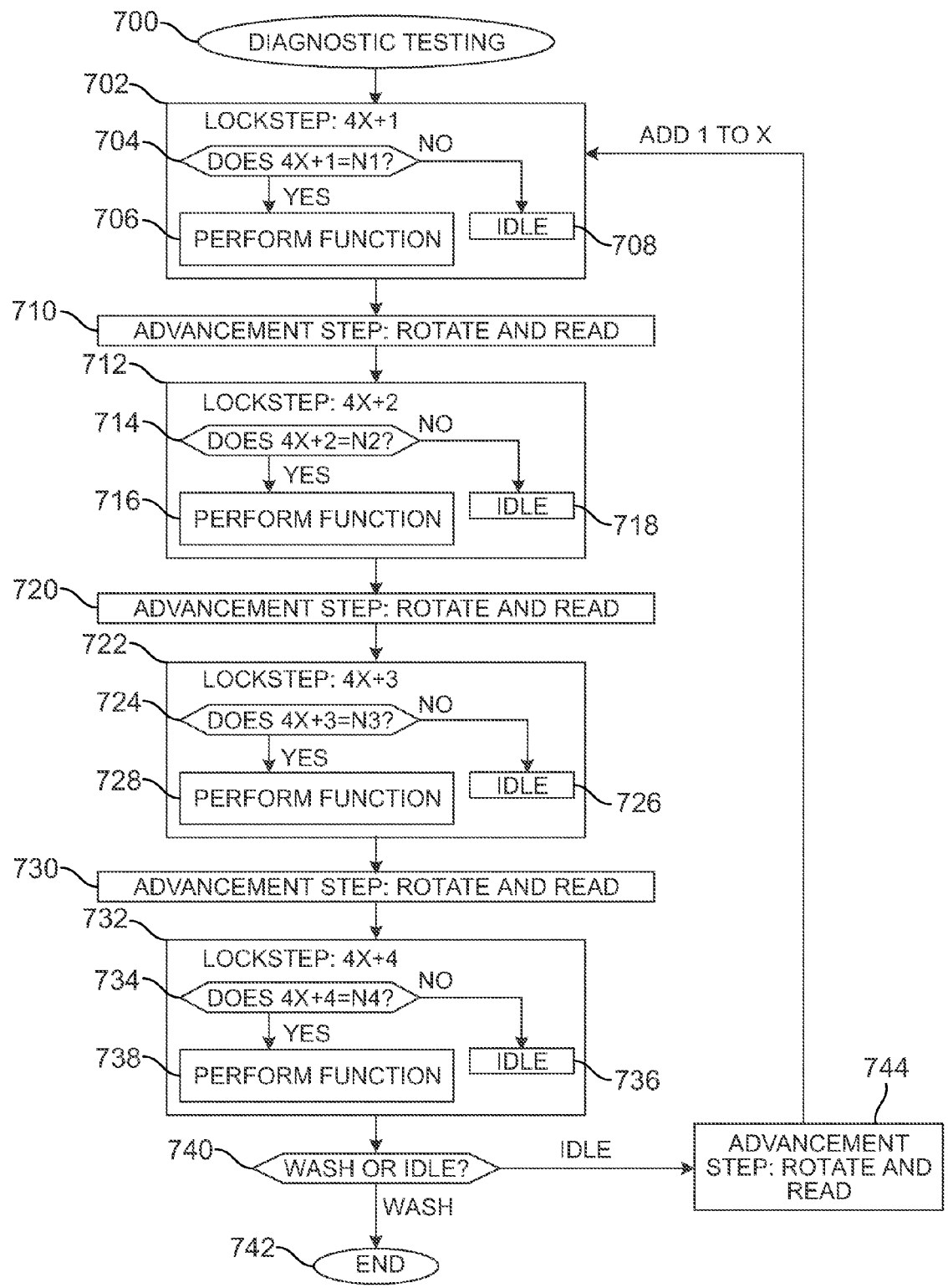
FIG. 7 is a flowchart illustrating an example diagnostic testing process.

A flowchart representative of an example method 700 for implementing the analyzers 100, 500 and/or the processing system 600 of FIGS. 1-6 is shown in FIG. 7. In this example, the method may be implemented as machine readable instructions comprising a program for execution by a processor such as the processor 912 shown in the example processor platform 900 discussed below in connection with FIG. 9. The program may be embodied in software stored on a tangible computer readable storage medium such as a CD-ROM, a floppy disk, a hard drive, a digital versatile disk (DVD), a Blu-ray disk, or a memory associated with the processor 912, but the entire program and/or parts thereof could alternatively be executed by a device other than the processor 912 and/or embodied in firmware or dedicated hardware. Further, although the example program is described with reference to the flowchart illustrated in FIG. 7, many other methods of implementing the example analyzers 100, 500 and/or processing system 600 may alternatively be used. For example, the order of execution of the blocks may be changed, and/or some of the blocks described may be changed, eliminated, or combined.

As mentioned above, the example process 700 of FIG. 7 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals. As used herein, "tangible computer readable storage medium" and "tangible machine readable storage medium" are used interchangeably. Additionally or alternatively, the example process 700 of FIG. 7 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable device or disk and to exclude propagating signals. As used herein, when the phrase "at least" is used as the transition term in a preamble of a claim, it is open-ended in the same manner as the term "comprising" is open ended.

FIG. 7 illustrates the example process 700 for diagnostic testing, which may be implemented, for example, by the example analyzers 100, 500 and/or the processing system 600 disclosed herein. The example process 700 of FIG. 7 is described from the perspective of the operations for a single reaction vessel as the reaction vessel rotates on a carousel of an analyzer throughout multiple locksteps. However, the example process 700 is repeatedly implemented simultaneously and/or in sequence for multiple reaction vessels. The example diagnostic testing may be, for example, a clinical chemistry test. The example analyzer 100 disclosed above includes a reaction carousel (e.g., the second carousel 104) having a plurality of reaction vessels. In some examples, the reaction carousel has 187 reaction vessels (e.g., glass cuvettes) spaced around the outer circumference of the second carousel. The reaction carousel rotates in locksteps (e.g., discrete intervals). Each lockstep, the reaction carousel is rotated about a quarter (e.g., 90°) rotation in the counterclockwise direction. In this example, in each lockstep, the reaction carousel rotates (e.g., via a motor) for one second and remains idle (e.g., stationary) for three seconds.

In the example process 700, the number of complete rotations of the reaction carousel is represented by the variable X, which is set to 0 at the beginning of the example process 700, and a predetermined timing of a function or test operation to be performed is represented by N1, N2, N3 and N4. In particular, in this example, N1, N2, N3 and N4 are integers that represent numbers of elapsed locksteps to be used to trigger the performance of a respective function or test operation. In other words, when N1 locksteps have elapsed or completed, a first function or test operation may be performed, when N2 lockstep have elapsed or completed, a second function or test operation may be performed and so on. As mentioned above, the reaction carousel has a lockstep rotation that is slightly more than a quarter turn. In some examples, the rotation is such that after four locksteps, or one full rotation, a given reaction vessel will be indexed one position past where the reaction vessel was in the previous rotation.

The example process includes $lockstep_{4X+1}$ (block 702). At the beginning, when a full rotation has not yet occurred, X is zero, and this is the first lockstep (i.e., $lockstep_{(4*0)+1}$). In this first lockstep, a function is performed on the reaction vessel if 4X+1=N1 (block 704). As noted above, N1 represents the timing or lockstep at which a specific function or test operation is performed in connection with the reaction vessel. For example, in the example analyzer 100 disclosed above, the third pipetting mechanism 150 is disposed near the reaction carousel 104 and is to dispense a sample into a reaction vessel at point C. In some examples, the first lockstep of a given test in a given reaction vessel occurs when the reaction vessel is at point C. Therefore, the function of dispensing sample, N1, may be set to 1, such that if this is the first lockstep (block 704) for the reaction vessel, the function is performed (block 706) (i.e., sample is dispensed into the reaction vessel) because 4X+1=N1 (e.g., (4*0)+1=1). In subsequent rotations, wherein N1 continues to be set to 1, and X is not zero, the reaction vessel is idle (block 708) and, for example, no functions are performed on the reaction vessel by the operator or robotic mechanisms of the example analyzer 100, 500 at this lockstep because 4X+1≠N1 (e.g., (4*1)+1≠1). Thus, in this example, if the function is to occur only at the first lockstep (e.g., dispensing a sample), then the example system will sit idle during each subsequent occurrence of a first lockstep during subsequent rotations (e.g., when X>1) until, for example, the reaction vessel is washed and ready for a subsequent test and X is reset to zero for the subsequent implementation of the example process 700.

The example process 700 includes advancing to the next lockstep (block 710) and reading (e.g., analyzing) the contents of any reaction vessel passing the reader. As mentioned above, the reaction carousel rotates about a quarter rotation every lockstep. In some examples, the reaction carousel is rotated for about one second of the four second lockstep time. During the advancement in this lockstep, about a quarter of the reaction vessels on the reaction carousel are passed in front of an analyzer (e.g., the analyzer 158) where the contents of the reaction vessels are analyzed. During the first few locksteps, all or most of the reaction vessels may be empty. However, in some examples, the reader continues to read, even if the data acquired is not used. By reading during every lockstep, the reader acquires a full range of readings during each reaction as the reactions are taking place. In other examples, the reader may delay reading for a predetermined amount of time and/or after a predetermined number reaction vessels are filled with sample and/or reagent.

The example process includes $lockstep_{4X+2}$ (block 712). Assuming one full rotation has not yet occurred, X is zero and this is the second lockstep (i.e., $lockstep_{(4*0)+2}$). During this second lockstep, a second function or test operation may be performed in connection with the reaction vessel if 4X+2=N2 (block 714). Similar to N1, N2 represents the specific timing of a specific function or test operation to be performed in connection with the reaction vessel. For example, in the example analyzer 100 disclosed above, the second pipetting mechanism 140 is disposed near the second carousel 104 and dispenses a first reagent into reaction vessels at point B. In some examples, the first carousel 102 includes an outer annular array of containers such as, for example, reagents used for first reagent. The second pipetting mechanism 140 aspirates from one of the containers on the outer annular array of containers and dispenses the liquid into a reaction vessel on the second carousel 104 at point B. In some examples, a reagent is to be dispensed into a reaction vessel during the second lockstep, wherein the first lockstep included adding sample to that reaction vessel. Therefore, for the function of dispensing a first reagent, N2 may be set to 2, such that if this is the second lockstep (block 714) for the reaction vessel, the function is performed (block 716), and a first reagent is dispensed into the reaction vessel (block 716) because $4X+2=N2$ (e.g., $(4*0)+2=2$). If X is not zero such as, for example, during subsequent rotations, then the reaction vessel is idle (block 718) and, for example, no functions are performed on the reaction vessel by the operator or robotic mechanisms of the example analyzer 100, 500 at this lockstep because $4X+2 \neq N2$ (e.g., $(4*1)+2 \neq 2$). Thus, in this example, if the function is to occur only at the second lockstep (e.g., dispensing a first reagent), then the example system will sit idle during each subsequent occurrence of a second lockstep during subsequent rotations until, for example, the reaction vessel is washed and ready for a subsequent test and X is reset to zero for the subsequent implementation of the example process 700.

The example process 700 includes advancing to the next lockstep (block 720) and reading (e.g., analyzing) the contents the reaction vessel. During the advancement in this lockstep, about a quarter of the reaction vessels are passed in front of an analyzer (e.g., the analyzer 158) where the contents of the reaction vessels are analyzed.

The example process includes lockstep$_{4X+3}$ (block 722). Assuming one full rotation has not yet occurred, X is zero and this is the third lockstep (i.e., lockstep$_{(4*0)+3}$). During this third lockstep, a third function or test operation may be performed in connection with the reaction vessel if $4X+3=N3$ (block 724). Similar to N1 and N2, N3 represents the specific timing or lockstep of a specific function or test operation to be performed in connection with the reaction vessel. For example, in the example analyzer 100 disclosed above, a first pipetting mechanism 130 is disposed within the second diameter 120 of the second carousel 104 and is to dispense a second reagent into reaction vessels on the second carousel 104 point A. In some examples, the first carousel 102 includes an inner annular array of containers 110a-n such as, for example, reagents used for a second reagent. The first pipetting mechanism 130 aspirates from one of the containers on the inner annular array of containers 110a-n and dispenses the liquid into a reaction vessel at point A. Therefore, the function of dispensing a second reagent may be activated for a particular vessel by setting N3 to any number of locksteps. In some examples, a diagnostic test includes adding a sample to a reaction vessel, adding a first reagent to the reaction vessel, and then incubating for a certain amount of time before dispensing the second reagent. In some examples, N3 can be set to 79, such that the reaction vessel will be at the $79^{th}$ lockstep, or third lockstep of the $19^{th}$ rotation of a testing (i.e., X=19) when the second reagent is added. Assuming each lockstep is about four seconds, the contents of the reaction vessel incubate for about five minutes before a second reagent is dispensed into the reaction vessel. Therefore, the function of dispensing a second reagent may be triggered by setting N3 to 79 so that at the $79^{th}$ lockstep (block 724), the function is performed (block 728) and a second reagent is dispensed into the reaction vessel because $4X+3=N3$ (e.g., $(4*19)+3=79$). If X is not 19 such as, for example, during previous rotations or subsequent rotations, then the reaction vessel is idle (block 726) and, for example, no functions are performed on the reaction vessel by the operator or robotic mechanism of the example analyzer 100, 500 at this lockstep because $4X+3 \neq N3$ (e.g., $(4*0)+3 \neq 79$). Thus, in this example, if the function is to occur only at the $79^{th}$ lockstep, i.e., the third lockstep of the $19^{th}$ rotation (e.g., dispensing a second reagent), then the example system will sit idle during each previous and subsequent occurrence of the third lockstep during previous and subsequent rotations until, for example, the reaction vessel is washed and ready for a subsequent test and X is reset to zero for the subsequent implementation of the example process 700.

The example process 700 includes advancing to the next lockstep (block 730) and reading (e.g., analyzing) the contents the reaction vessels that pass the reader.

The example process includes lockstep$_{4X+4}$ (block 732). At the beginning, when a full rotation has not occurred yet, X is zero and this is the fourth lockstep (i.e., lockstep$_{(4*0)+4}$). (block 732). During this fourth lockstep, another function or test operation may be performed in connection with the reaction vessel if $4X+4=N4$ (block 734). Similar to N1, N2 and N3, N4 represents the specific timing of a specific function or test operation to be performed on the reaction vessel. For example, in the example analyzer 100 disclosed above, the wash zone 162 is disposed to wash reaction vessels at point D. In some examples, a reaction vessel is washed after a test has finished in the reaction vessel. Therefore, N4 can be set at any number to trigger the washing of a vessel. In some examples, a full test of a given sample occurs over about 37 full rotations of the carousel. Therefore, N4 may be set to 152, such that when X=37, the reaction vessel is washed (block 738) because $4X+4=N3$ (e.g., $(4*38)+4=156$). If X is not 37 such as, for example, during the previous 36 rotations, then the reaction vessel is idle (block 736) and, for example, no functions are performed on the reaction vessel by the operator or any robotic mechanism of the example analyzer 100, 500 at this lockstep because $4X+4 \neq N4$ (e.g., $(4*0)+4 \neq 156$). Thus, in this example, if the function is to occur only at the $156^{th}$ lockstep, i.e., the fourth lockstep of the $37^{th}$ rotation (e.g., washing a reaction vessel), then the example system will sit idle during each previous occurrence of the fourth lockstep during previous rotations. Once the reaction vessel is washed and ready for a subsequent test and X is reset to zero for the subsequent implementation of the example process 700.

As noted above, in some examples, if the reaction vessel is washed (block 740), the process 700 ends (block 742) and may start over with a clean reaction vessel for a subsequent test. If the diagnostic testing is not complete, the reaction vessel is idle (block 740), and the reaction carousel advances to the next lockstep (block 744). The example process includes continuing with lockstep$_{4X+1}$ (block 702), where "1" has been added to X because one full rotation has occurred. Therefore, the start of the second rotation, i.e., the first lockstep of the second rotation will be the fifth lockstep (i.e., lockstep$_{(4*1)+1}$) (block 702). This process 700 may continue as many times as determined by the testing protocols and scheduling sequences.

Additionally, this example is viewed from the perspective of one reaction vessel progressing through a diagnostic test. However, multiple other reactions may be occurring during the same locksteps and may be performed using this process as well. Although the lockstep triggers N1, N2, N3 and N4 are described above as being associated with adding a sample, a first reagent, a second reagent, and a wash zone, respectively, N1-N4 may be associated with any function, test operation or instrument used in diagnostic testing such as, for example, an in track vortexer (e.g., a mixer), an incubator (e.g., a heat source), etc. Therefore, the process 700 allows a diagnostic test to be customized in regards to the timing and sequencing of the various functions to be performed in connection with one or more vessels and samples disposed therein.

Additionally, this example includes functions N1, N2, N3, and N4, for the respective locksteps during each rotation. However, in other examples, more than one function can be arranged at the each lockstep and distinguished by the number of rotations completed. For example, a first function may be performed during the first lockstep of the first rotation and a second function may be performed during the fifth lockstep (i.e., the first lockstep of the second rotation).

Figure 8:
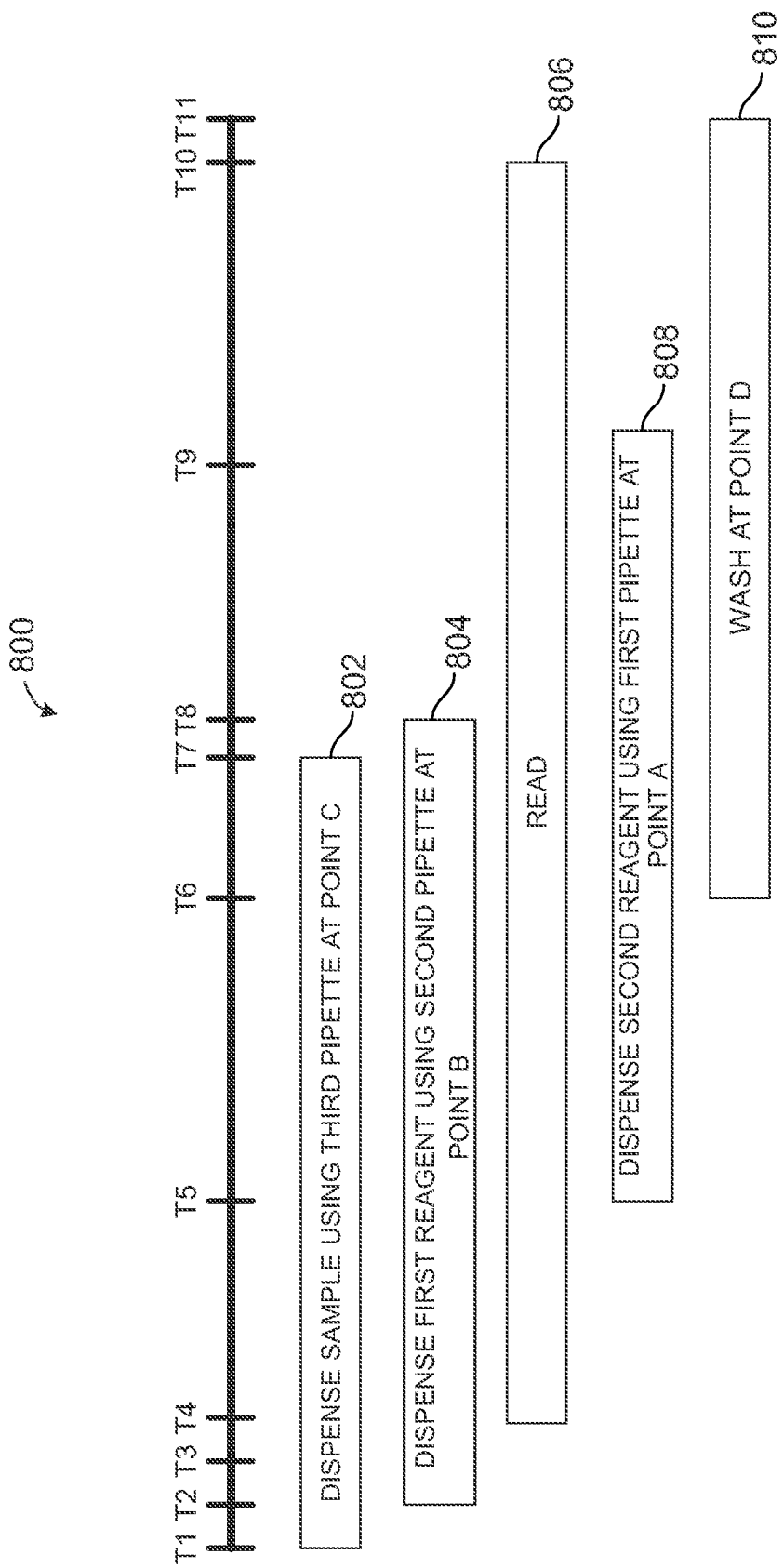
FIG. 8 is a timeline illustrating timing sequences of various components in the example analyzer shown in FIGS. 1-4.

FIG. 8 illustrates an example timeline 800 that represents the timing of use for a number of specific functions performed during a diagnostic test such as, for example, those performed in the example analyzers 100, 500 disclosed above. The example analyzer 100 disclosed above includes the third pipetting mechanism 150 for dispensing sample at point C, the second pipetting mechanism 140 for dispensing a first reagent at point B, the first pipetting mechanism 130 to dispense a second reagent at point B, and the wash zone 162 to wash a reaction vessel at point D. For illustrative purposes, it is assumed that a number of tests are to be performed sequentially and/or concurrently starting with the first sample being dispensed into a first reaction vessel at T1. In some examples, the reaction carousel rotates in discrete locksteps. Every lockstep, the third pipetting mechanism dispenses a sample into a reaction vessel at point C 802. As shown, this function continues from T1 to T7. For example, if 187 tests are to be performed in 187 reaction vessels on the reaction carousel, then the third pipetting mechanism dispenses one sample into each reaction vessel at every lockstep until all the samples have been dispensed. Therefore, in some examples, T7 may represent the timing of when or the lockstep at which the last sample is dispensed into a reaction vessel.

The example timeline 800 also includes dispensing a first reagent using the second pipetting mechanism at point B 804. As mentioned above, in some examples, a first reagent is to be dispensed into a reaction vessel that was previously at point C (i.e., a reaction vessel including a sample). In this example, the second pipetting mechanism begins dispensing a first reagent to a reaction vessel at point B at time or lockstep T2. In this example, T2 may be one lockstep after the lockstep during which sample is added to the first reaction vessel. The second pipetting mechanism continues to dispense the first reagent until T8, which may be, for example, one lockstep after the last sample is dispensed into the last reaction vessel (i.e., once a first reagent has been added to every sample).

The example timeline 800 includes reading 806 the reaction vessels. In some examples, the reader analyzes the reaction vessels as the reaction vessels pass in front of the reader during the advancement portion of the lockstep. Therefore, assuming that each lockstep rotation is a about quarter rotation, and the reaction carousel has 187 reaction vessels, about 47 reaction vessels pass in front of the reader during each lockstep. During the first few locksteps of a diagnostic test, all or a majority of the reaction vessels passing in front of the reader are empty. Therefore, as shown in this example, the reader begins reading at time or lockstep T4, which may be, for example, when the first reaction vessel having a sample and a reagent passes in front of the reader. During every rotation, each reaction vessel is analyzed. In some examples, a full diagnostic test requires 38 reads and, thus, 38 full rotations. Therefore, the reader continues to read until T10, which may be, for example, when the last reaction vessel that was dispensed to has been read 38 times.

The example timeline 800 includes dispensing a second reagent 808, via the first pipetting mechanism, beginning at time or lockstep T5. In some examples, a test sample and a first reagent react for a period of time and then a second reagent is added. To ensure adequate incubation time, the second reagent may be dispensed after a set period of time or number of locksteps, T5. Starting at T5, the first pipetting mechanism dispenses a second reagent into the reaction vessels at point A. This continues until T9, which may be, for example, when the last reaction vessel reaches point A and, thus, all the reaction vessels have had a second reagent dispensed therein.

The example timeline 800 also includes a wash at point D 810. In the example analyzer 100, the wash zone 162 washes reaction vessels at point D. As mentioned above, some reactions may occur over 38 full rotations. After the 38$^{th}$ rotation, the reaction is to be washed out of the reaction vessel. Therefore, the wash begins at T6, which may be, for example, the time or lockstep at which the first reaction vessel has completed its full 38 rotation testing. The wash 810 continues to wash each vessel until T11, which may be, for example, when the last reaction completes its 38 rotation test.

The functions illustrated in FIG. 8 may operate simultaneously as the reaction carousel rotates, and different timing sequencing may be determined based on the types of tests to be conducted and the types of procedures to be performed. In addition, the functions may operate continually. For example, if a first reaction vessel is washed at T7, sample may be dispensed into that first reaction vessel at T8 for a subsequent test, and the remaining functions also may continue.

Figure 9:
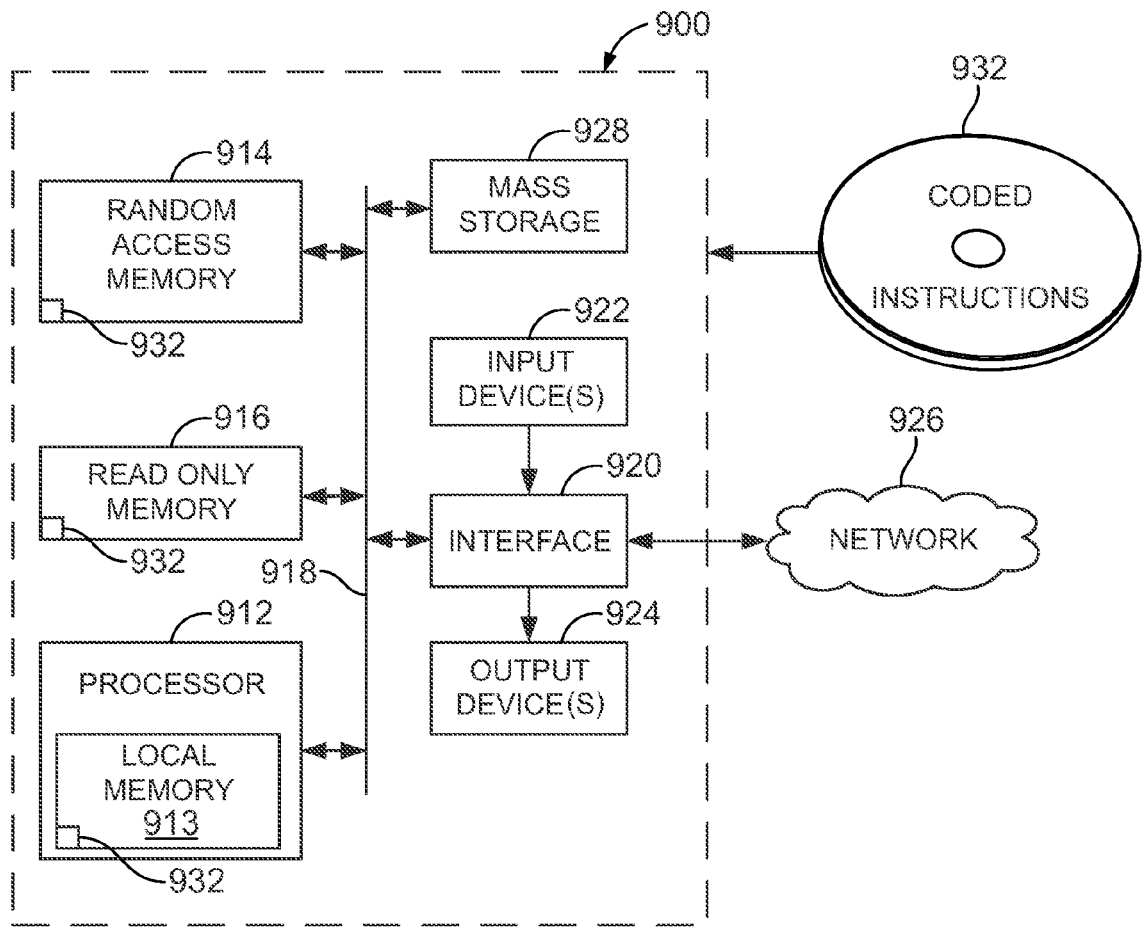
FIG. 9 is a diagram of a processor platform that may be used with the examples disclosed herein.

FIG. 9 is a block diagram of an example processor platform 900 capable of executing the one or more instructions of FIG. 7 to implement one or more portions of the apparatus and/or systems of FIGS. 1-6. The processor platform 900 can be, for example, a server, a personal computer, a mobile device (e.g., a cell phone, a smart phone, a tablet such as an iPad™), a personal digital assistant (PDA), an Internet appliance, and/or or any other type of computing device.

The processor platform 900 of the illustrated example includes a processor 912. The processor 912 of the illustrated example is hardware. For example, the processor 912 can be implemented by one or more integrated circuits, logic circuits, microprocessors or controllers from any desired family or manufacturer.

The processor 912 of the illustrated example includes a local memory 913 (e.g., a cache). The processor 912 of the illustrated example is in communication with a main memory including a volatile memory 814 and a non-volatile memory 916 via a bus 918. The volatile memory 914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 916 may be implemented by flash memory and/or any other desired type of memory device. Access to the main memory 914, 916 is controlled by a memory controller.

The processor platform 900 of the illustrated example also includes an interface circuit 920. The interface circuit 920 may be implemented by any type of interface standard, such as an Ethernet interface, a universal serial bus (USB), and/or a PCI express interface.

In the illustrated example, one or more input devices 922 are connected to the interface circuit 920. The input device(s) 922 permit(s) a user to enter data and commands into the processor 912. The input device(s) can be implemented by, for example, an audio sensor, a microphone, a camera (still or video), a keyboard, a button, a mouse, a touchscreen, a trackpad, a trackball, isopoint and/or a voice recognition system.

One or more output devices 924 are also connected to the interface circuit 920 of the illustrated example. The output devices 924 can be implemented, for example, by display devices (e.g., a light emitting diode (LED), an organic light emitting diode (OLED), a liquid crystal display, a cathode ray tube display (CRT), a touchscreen, a tactile output device and/or a light emitting diode (LED). The interface circuit 920 of the illustrated example, thus, typically includes a graphics driver card, a graphics driver chip or a graphics driver processor.

The interface circuit 920 of the illustrated example also includes a communication device such as a transmitter, a receiver, a transceiver, a modem and/or network interface card to facilitate exchange of data with external machines (e.g., computing devices of any kind) via a network 926 (e.g., an Ethernet connection, a digital subscriber line (DSL), a telephone line, coaxial cable, a cellular telephone system, etc.).

The processor platform 900 of the illustrated example also includes one or more mass storage devices 928 for storing software and/or data. Examples of such mass storage devices 928 include floppy disk drives, hard drive disks, compact disk drives, Blu-ray disk drives, RAID systems, and digital versatile disk (DVD) drives.

Coded instructions 932 to implement the method of FIG. 7 may be stored in the mass storage device 928, in the volatile memory 914, in the non-volatile memory 916, and/or on a removable tangible computer readable storage medium such as a CD or DVD.

The example analyzers 100 and 500 described herein locate a first carousel beneath a second carousel, thereby reducing the footprint (e.g., width and length dimensions) of the analyzer. The example analyzers 100 and 500 also locate pipetting mechanisms within the dimensions of the first and/or second carousel to reduce the footprint and distance traveled by the pipetting mechanisms. Additionally, by reducing the footprint of the analyzer, the carousels may be relatively wider (e.g., having a greater diameter) and/or high and, thus, include more containers (e.g., reagents) to perform more tests.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
a first carousel rotatably coupled to a base, the first carousel having a first axis of rotation;
a second carousel rotatably coupled to the base and vertically spaced over the first carousel such that at least a portion of the second carousel is disposed over the first carousel, the second carousel having a second axis of rotation and a plurality of vessels; and
a first pipetting mechanism rotatable about a third axis of rotation, the third axis of rotation offset from the second axis of rotation, the third axis of rotation disposed within a first circumference of the first carousel and a second circumference of the second carousel, the first pipetting mechanism to access the first carousel and the second carousel.

2. The apparatus of claim 1, wherein the first axis of rotation and the second axis of rotation are parallel to and offset from each other.

3. The apparatus of claim 1, wherein the first carousel has a first diameter and the second carousel has a second diameter less than the first diameter.

4. The apparatus of claim 1 further comprising a second pipetting mechanism to access the first carousel and the second carousel.

5. The apparatus of claim 4, wherein the first carousel comprises an outer annular array of containers and an inner annular array of containers concentric with the outer annular array and the first pipetting mechanism is to access at least one of the inner annular array of containers or the vessels, and the second pipetting mechanism to access at least one of the outer annular array of containers or the vessels.

6. The apparatus of claim 5, wherein the first pipetting mechanism comprises a first pipette arm rotatable along a first path of travel over a first inner container of the inner annular array of containers and a first vessel of the plurality of vessels, and the second pipetting mechanism comprises a second pipette arm rotatable along a second path of travel over a second outer container of the outer annular array of containers and a second vessel of the plurality of vessels.

7. The apparatus of claim 4, wherein the second pipetting mechanism is rotatable about a fourth axis of rotation, the fourth axis of rotation offset from the first axis of rotation.

8. The apparatus of claim 4 further comprising a third pipetting mechanism to access the second carousel and not access the first carousel.

9. The apparatus of claim 8, wherein the third pipetting mechanism comprises a third pipette arm rotatable along a third path of travel over a container outside of a first circumference of the first carousel and a second circumference of the second carousel and over a third vessel of the plurality of vessels.

10. The apparatus of claim 1 further comprising a plate coupled to the base disposed between the first carousel and the second carousel, the second carousel being rotatably coupled to the plate.

11. The apparatus of claim 10, wherein the first pipetting mechanism is coupled to the plate.

12. The apparatus of claim 1, wherein the first carousel comprises an outer annular array of containers, an inner annular array of containers concentric with the outer annular array and a middle annular array of containers spaced radially between the outer annular array of containers and the inner annular array of containers.

13. The apparatus of claim 1, wherein the second carousel is to rotate in a plurality of intervals, each interval comprising an advancement and a stop.

14. The apparatus of claim 13, wherein the second carousel is operable to rotate approximately 90° during the advancement of one of the intervals.

15. The apparatus of claim 13, wherein the second carousel is stationary during the stop of one of the intervals, a duration of the stop being greater than a duration of the advancement of the interval.

16. The apparatus of claim 1, wherein the first carousel is to rotate in a plurality of intervals, each interval comprising an advancement and a stop.

17. The apparatus of claim 16, wherein the first carousel is operable to rotate approximately 180° during the advancement of one of the intervals, a duration of the advancement being about one second of the interval.

18. The apparatus of claim 1, wherein the first carousel comprises an outer annular array of containers that contain a first type of reagent and an inner annular array of containers concentric with the outer annular array that contain a second type of reagent different than the first type of reagent.

19. The apparatus of claim 1, wherein the first carousel includes a plurality of reagent containers, and wherein the vessels of the second carousel are reaction vessels.

20. The apparatus of claim 1, further comprising:
a second pipetting mechanism rotatable about a fourth axis of rotation, the fourth axis of rotation disposed within the first circumference and outside of the second circumference; and a third pipetting mechanism rotatable about a fifth axis of rotation, the fifth axis of rotation disposed outside of the first circumference and outside of the second circumference.

21. An apparatus comprising:
a reagent carousel rotatably coupled to a base about a first axis of rotation;
a reaction carousel rotatably coupled to the base about a second axis of rotation, the reaction carousel disposed above the reagent carousel, the reaction carousel defining an annular rack having a bore; and
a first pipette rotatable about a third axis of rotation defined by a base assembly, the base assembly of the first pipette extending through the bore of the reaction carousel, the first pipette movable to a first position to be in fluid communication with a reagent container disposed on the reagent carousel and to a second position to be in fluid communication with a reaction vessel disposed on the reaction carousel.

22. The apparatus of claim 21, wherein the first axis of rotation and the second axis of rotation are parallel to and offset from each other.

23. The apparatus of claim 21, wherein the reagent container has a reagent, the first pipette to aspirate at least a portion of the reagent from the reagent container, move upward vertically, then dispense the portion of the reagent into the reaction vessel.

24. The apparatus of claim 21 further comprising a second pipette to aspirate a sample from a sample container apart from the reagent carousel and the reaction carousel and dispense the sample into the reaction vessel.

25. A method comprising:
rotating a first carousel relative to a base about a first axis of rotation, the first carousel having an outer annular array of containers and an inner annular array of containers concentric with the outer annular array;
rotating a second carousel relative to the base about a second axis of rotation, the second carousel having a plurality of vessels and being vertically spaced over the first carousel such that at least a portion of the second carousel is disposed over the first carousel;
rotating a first pipetting mechanism about a third axis of rotation, the third axis of rotation offset from the second axis of rotation, the third axis of rotation disposed within a circumference of the first carousel; and
aspirating a first fluid from the first carousel via the first pipetting mechanism.

26. The method of claim 25, wherein the first axis of rotation and the second axis of rotation are parallel to and offset from each other.

27. The method of claim 25, wherein the first carousel has a first diameter and the second carousel has a second diameter less than the first diameter.

28. The method of claim 25 further comprising aspirating a second fluid from the first carousel via a second pipetting mechanism.

29. The method of claim 28 further comprising:
accessing at least one of the inner annular array of containers or the vessels with the first pipetting mechanism; and
accessing at least one of the outer annular array of containers or the vessels with the second pipetting mechanism.

30. The method of claim 29 further comprising:
rotating a first pipette arm of the first pipetting mechanism along a first path of travel over a first inner container of the inner annular array of containers and a first vessel; and
rotating a second pipette arm of the second pipetting mechanism along a second path of travel over a first outer container of the outer annular array of containers and a second vessel.

31. The method of claim 28, wherein the second pipetting mechanism is rotatable about a fourth axis of rotation, the fourth axis of rotation offset from the first axis of rotation.

32. The method of claim 28 further comprising aspirating a third fluid via a third pipetting mechanism.

33. The method of claim 32 further comprising rotating a third pipette arm of the third pipetting mechanism along a third path of travel over a container outside of a first circumference of the first carousel and a second circumference of the second carousel and over a third vessel of the plurality of vessels.

34. The method of claim 25 further comprising rotating the second carousel in a plurality of intervals, each interval comprising an advancement and a stop.

35. The method of claim 34 further comprising rotating the second carousel approximately 90° during the advancement of one of the intervals.

36. The method of claim 34 further comprising idling the second carousel during the stop of one of the intervals, a duration of the stop being greater than a duration of an advancement of the interval.

37. The method of claim 25 further comprising:
accessing a first vessel on the second carousel with the first pipetting mechanism;
rotating the second carousel in a plurality of intervals; and
rotating the second carousel for two or more intervals for the first pipetting mechanism to access a second vessel, the second vessel being physically adjacent to the first vessel.

38. The method of claim 25 further comprising rotating the first carousel in a plurality of intervals, each interval comprising an advancement and a stop.

39. The method of claim 38 further comprising rotating the first carousel approximately 180° during the advancement of one of the intervals, a duration of the advancement being about one second of the interval.

40. The method of claim 25 further comprising activating a servo motor to rotate one or more of the first carousel or the second carousel.

41. The apparatus of claim 1, wherein the first pipetting mechanism comprises a probe arm having a vertically descending portion.

* * * * *